US010269198B2

(12) United States Patent
Saso et al.

(10) Patent No.: US 10,269,198 B2
(45) Date of Patent: Apr. 23, 2019

(54) SUSPICIOUS PERSON REPORT SYSTEM AND SUSPICIOUS PERSON REPORT METHOD

(71) Applicant: Panasonic Intellectual Property Management Co., Ltd., Osaka (JP)

(72) Inventors: Atsushi Saso, Kanagawa (JP); Takamichi Matsusako, Tokyo (JP); Naomi Tomiyama, Kyoto (JP); Akira Asai, Osaka (JP); Mikiko Matsuo, Nara (JP); Yuichi Aoki, Osaka (JP); Motoji Ohmori, Osaka (JP); Eiichiro Okuda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/681,922

(22) Filed: Aug. 21, 2017

(65) Prior Publication Data

US 2018/0061159 A1 Mar. 1, 2018

(30) Foreign Application Priority Data

Aug. 29, 2016 (JP) ................................ 2016-166722
Aug. 30, 2016 (JP) ................................ 2016-167550

(51) Int. Cl.
*A61B 5/16* (2006.01)
*G07C 9/00* (2006.01)
(Continued)

(52) U.S. Cl.
CPC ..... *G07C 9/00158* (2013.01); *G08B 13/19645* (2013.01); *A61B 5/16* (2013.01); *G08B 31/00* (2013.01); *H04N 7/18* (2013.01)

(58) Field of Classification Search
None
See application file for complete search history.

(56) References Cited

U.S. PATENT DOCUMENTS 9,300,925 B1 * 3/2016 Zhang ............... H04N 7/181
2005/0105765 A1 * 5/2005 Han ............... G06K 9/00295
382/100
(Continued)

FOREIGN PATENT DOCUMENTS

JP 2007-179475 7/2007
JP 2007-249819 9/2007
(Continued)

OTHER PUBLICATIONS

Behera et al., Multi-Camera Based Surveillance System, 2012 World Congress on Information and Communication Technologies, 978-1-4673-4805-8/12/$31.00 c 2012 IEEE, pp. 102-108.*
(Continued)

*Primary Examiner* — Carlos Garcia
(74) *Attorney, Agent, or Firm* — Greenblum & Bernstein, P.L.C.

(57) ABSTRACT

A suspicious person report system includes: a biometric sensor detecting biometric data of a person in a first region; a presuming unit calculating, from the biometric data, a stress index and presuming that the person is a suspicious person when the calculated stress index is higher than a reference value; a first camera acquiring first image data of the person in the first region; a second camera acquiring second image data of the person in a second region, the second region being a route after the first region before a third region; a monitoring unit checking the second image data with the first image data corresponding to the suspicious person to thereby track the suspicious person in the second region and determine whether the suspicious person enters the third region; and a warning unit emitting a (Continued)

warning when the monitoring unit determines that the suspicious person enters the third region.

15 Claims, 21 Drawing Sheets

(51) Int. Cl.
*H04N 7/18* (2006.01)
*G08B 31/00* (2006.01)
*G08B 13/196* (2006.01)

(56) References Cited

U.S. PATENT DOCUMENTS

| | | | | |
|---|---|---|---|---|
| 2006/0056056 | A1* | 3/2006 | Ahiska | G08B 13/19608 359/690 |
| 2006/0170769 | A1* | 8/2006 | Zhou | G06K 9/00362 348/143 |
| 2008/0080748 | A1* | 4/2008 | Sukegawa | G06K 9/00288 382/118 |
| 2008/0292140 | A1* | 11/2008 | Morris | G06K 9/00295 382/103 |
| 2014/0152836 | A1* | 6/2014 | Morris | G08B 13/19608 348/159 |
| 2015/0061825 | A1 | 3/2015 | Suzuki et al. | |
| 2016/0210516 | A1* | 7/2016 | Kim | G06K 9/00751 |

FOREIGN PATENT DOCUMENTS

| | | |
|---|---|---|
| JP | 2012-120206 | 6/2012 |
| JP | 2015-046065 | 3/2015 |
| WO | 2001/093746 | 12/2001 |
| WO | 2005/055151 | 6/2005 |

OTHER PUBLICATIONS

Chew et al., A method and system for monitoring the movement of people, Sep. 21, 2013, IP.com, Publication No. TW I409705 B.*
Goswami, Facial recognition method to enhance airport security, Jun. 2, 2017, IP.com, Publication No. IN 874/DEL/2013 A.*
Weissenfeld et al., Security Components in a One-Stop-Shop Border Control System, 2014 IEEE Joint Intelligence and Security Informatics Conference, 978-1-4799-6364-5/14 $31.00 © 2014 IEEE DOI 10.1109/JISIC.2014.42, pp. 228-231.*
Essendorfer et al., An Integrated System for Border Surveillance, 2009 Fourth International Conference on Systems, 978-0-7695-3551-7/09 $25.00 © 2009 IEEE DOI 10.1109/ICONS.2009.27, pp. 96-101.*

* cited by examiner

| PASSPORT NUMBER | IMAGE DATA |
|---|---|
| YYY | |

FIG. 11
| USER ID | IMAGE DATA | RELATED SUSPICIOUS PERSON |
|---|---|---|
| XXX |  |  |

FIG. 13
| PASSPORT NUMBER | IMAGE DATA | RELATED SUSPICIOUS PERSON |
|---|---|---|
| YYY |  |  |

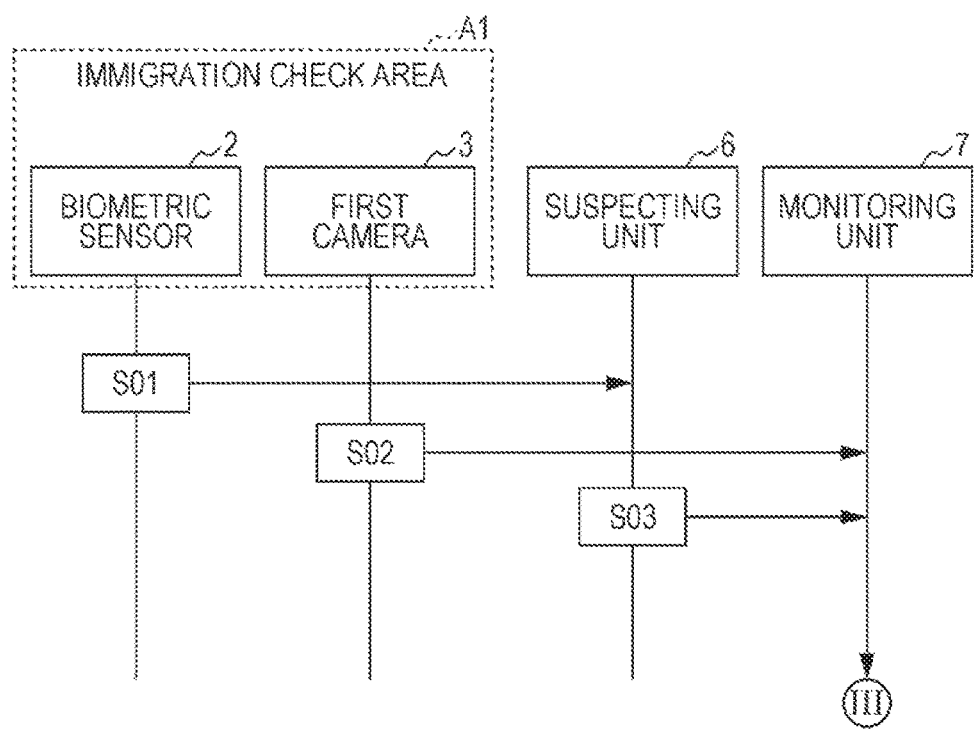

PASSPORT NUMBER

YYY

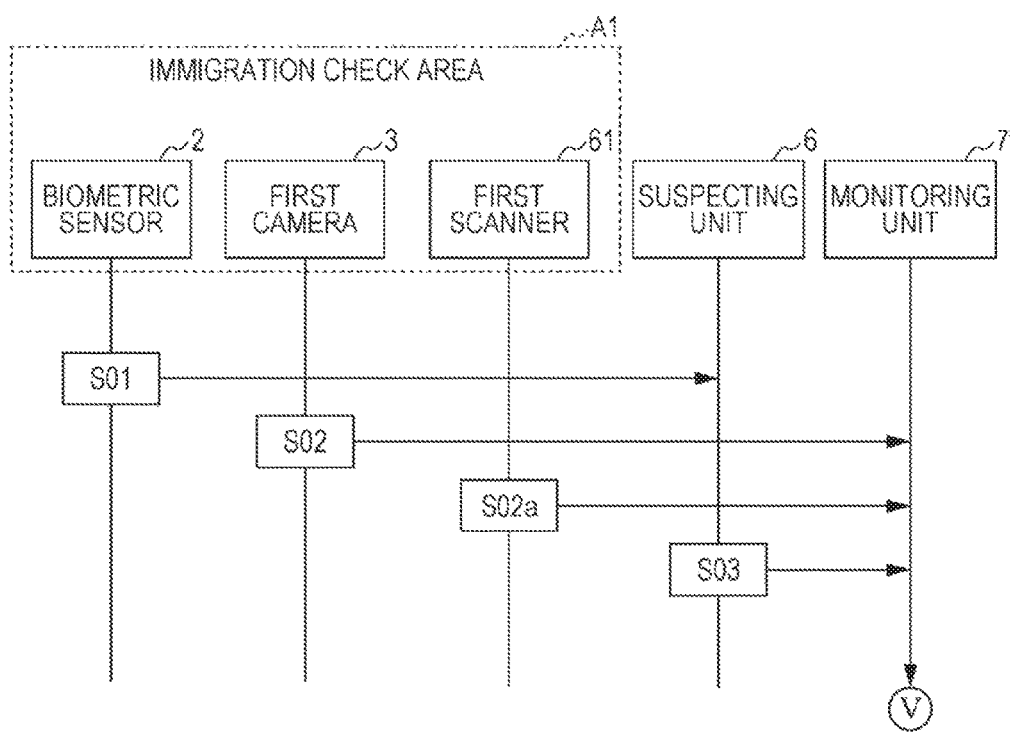

SUSPICIOUS PERSON REPORT SYSTEM AND SUSPICIOUS PERSON REPORT METHOD

BACKGROUND

1. Technical Field

The present disclosure relates to a technique of reporting a suspicious person, for example, in an airport.

2. Description of the Related Art

In recent years, there have been proposed various techniques of presuming an emotion of a person using vital data of the person. For example, Japanese Unexamined Patent Application Publication (Translation of PCT Application) No. 2003-534864 (P2003-534864A) discloses a technique for determining a psychological state of a person using thermal image data of the face of the person. P2003-534864A also proposes to use the technique to detect terrorists and smugglers.

SUMMARY

It is demanded to accurately determine a suspicious person in an airport and the like.

One non-limiting and exemplary embodiment provides the techniques described below.

In one general aspect, the techniques disclosed here feature a suspicious person report system, including: a biometric sensor that detects biometric data of a person in a first region; a presuming unit that calculates, from the biometric data, a stress index indicating a degree of stress and presumes that the person is a suspicious person when the calculated stress index is higher than a predetermined reference value; a first camera that acquires first image data including an image of the person in the first region; a second camera that acquires second image data including an image of the person in a second region, the second region being a route that the person passes after leaving the first region before entering a third region; a monitoring unit that checks the second image data with the first image data corresponding to the person presumed as the suspicious person to thereby track the person presumed as the suspicious person in the second region and determine whether or not the person presumed as the suspicious person enters the third region; and a warning unit that emits a warning when the monitoring unit determines that the person presumed as the suspicious person enters the third region.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 11 is a diagram showing a suspicious person management table according to the third embodiment;

FIG. 13 is a diagram showing a suspicious person management table according to a modification of the third embodiment;

FIG. 16 is a diagram showing an example of a suspicious person management table according to the fourth embodiment;

FIG. 17 is a sequence chart showing the operation of the suspicious person report system;

FIG. 24 is a diagram showing an example of a suspicious person management table according to the sixth embodiment;

FIG. 25 is a sequence chart showing the operation of the suspicious person report system according to the sixth embodiment.

Figure 1:
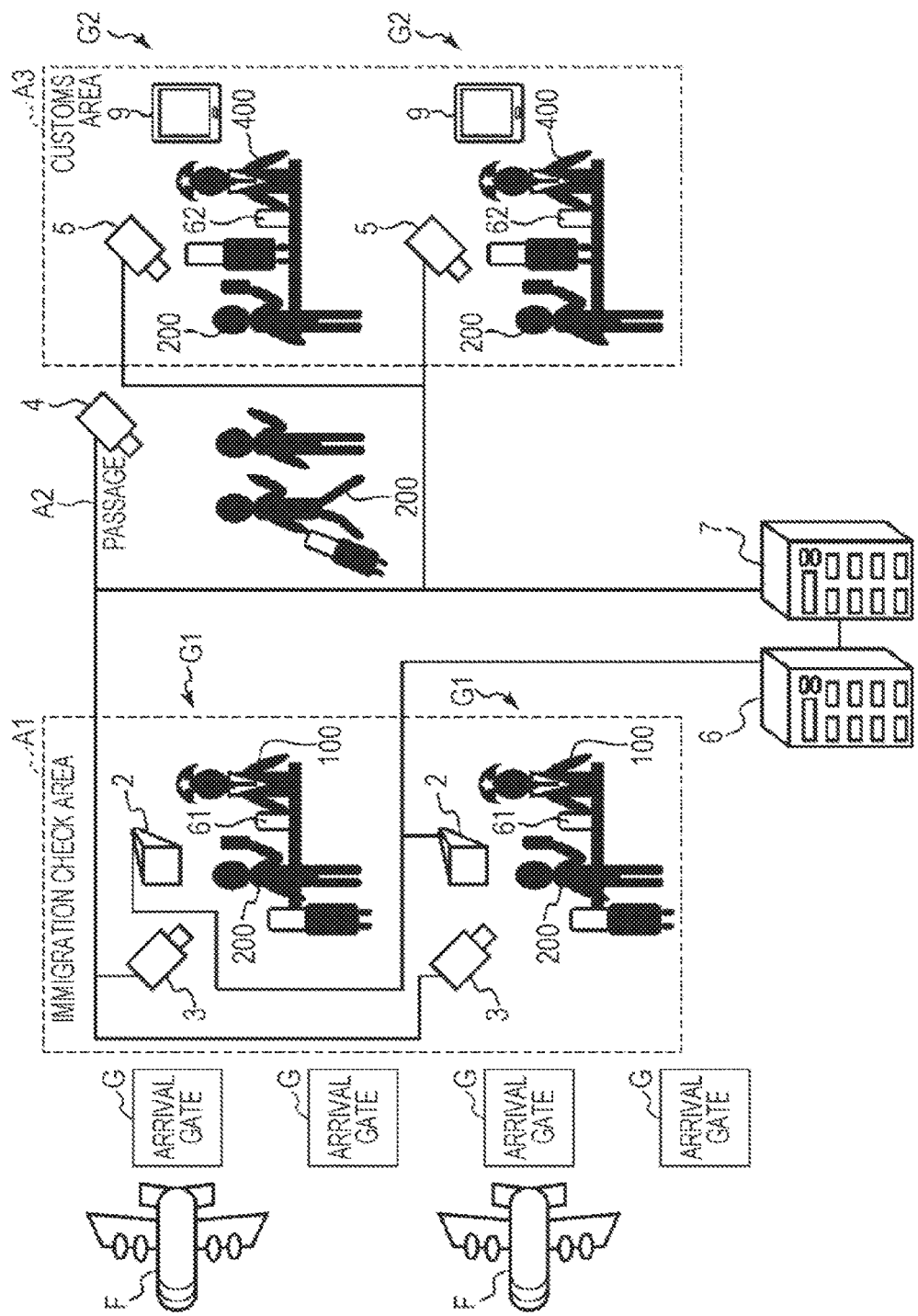
FIG. 1 is a schematic diagram of an airport to which a suspicious person report system according to an embodiment of the present disclosure is applied.

DETAILED DESCRIPTION (Underlying Knowledge Forming Basis of the Present Disclosure)

P2003-534864A discloses that use of a psychological state of each person determined based on a thermal image data of the person enables detection of a suspicious person such as a smuggler of drug in a border security point or a terrorist in a foreign facility.

In an airport, a port, or the like, in general, first, an entrant undergoes an immigration check in an immigration check area. Thereafter, in a customs area, the entrant is inspected as to whether the entrant is carrying a suspicious object.

However, P2003-534864A does not take into account at all, for example, two or more regions located apart from one another in the airport such as the immigration check area and the customs area where the entrant is obliged to pass in order. Therefore, this technique cannot find out a suspicious person by effectively using the two or more regions.

Even if the technique of P2003-534864A is applied in the immigration check area to attempt to arrest a suspicious person, there is a risk that immigration officers permit passage of a suspicious person in the immigration check area since the immigration officers need to check a large number of entrants. In this case, the technique of P2003-534864A cannot find out the suspicious person later because the technique does not involve recoding information on the suspicious person in a memory.

Further, it is also conceivable that an entrant performs suspicious behavior of handing a suspicious object to a different person on a route from the immigration check area to the customs area. Therefore, it is necessary to monitor suspicious people on the route as well.

However, P2003-534864A does not take the above issues into account at all, and therefore has a problem that suspicious behavior by a suspicious person on the route cannot be checked.

Under these circumstances, the present disclosure presents a technique capable of determining a suspicious person by effectively using two or more regions located apart from one another where an entrant is obliged to pass in order.

An overview of an aspect of the present disclosure is as described below.

[Item 1]
A suspicious person report system, including:
  a biometric sensor that detects biometric data of a person in a first region;
  a presuming unit that calculates, from the biometric data, a stress index indicating a degree of stress and presumes that the person is a suspicious person when the calculated stress index is higher than a predetermined reference value;
  a first camera that acquires first image data including an image of the person in the first region;
  a second camera that acquires second image data including an image of the person in a second region, the second region being a route that the person passes after leaving the first region before entering a third region;
  a monitoring unit that checks the second image data with the first image data corresponding to the person presumed as the suspicious person to thereby track the person presumed as the suspicious person in the second region and determine whether or not the person presumed as the suspicious person enters the third region; and
  a warning unit that emits a warning when the monitoring unit determines that the person presumed as the suspicious person enters the third region.

With the configuration of the item 1, the biometric data and the first image data of the person entering the first region are acquired. If the stress index obtained from the biometric data is higher than the reference value, the person is presumed as a suspicious person.

It is possible to monitor an action of the suspicious person in the second region as well by checking the second image data captured by the second camera set in the second region, where the suspicious person passes after leaving the first region, with the first image data concerning the person presumed as the suspicious person. When the suspicious person enters the third region through the second region, the warning is emitted.

Therefore, even if an officer permits passage of the suspicious person in the first region, the suspicious person can be found out since the warning is emitted when the suspicious person enters the third region. Therefore, it is possible to find out the suspicious person by effectively using two or more regions located apart from one another where a person is obliged to pass in order.

The action of the suspicious person can be monitored in the second region between the first region and the third region as well. Therefore, it is possible to check a suspicious action by the suspicious person in the second region by analyzing the second image data.

[Item 2]
The suspicious person report system according to the item 1, further including a third camera that acquires third image data including an image of the person in the third region, wherein
  the monitoring unit checks the third image data with the first image data and determines that the person presumed as the suspicious person enters the third region when the third image data includes an image of the person presumed as the suspicious person.

With the configuration of the item 2, the person entering the third region is captured as the third image data by the third camera set in the third region. When the third image data includes an image of a person image indicated by the first image data concerning the person presumed as the suspicious person, the warning is emitted. Therefore, even if the sight of the suspicious person is lost when the suspicious person enters the third region from the second region, it is possible to surely find out the suspicious person in the third region.

[Item 3]
The suspicious person report system according to the item 1, further including:
  a first acquirer that acquires a passport number of the person in the first region; and
  a second acquirer that acquires a passport number of the person in the third region, wherein
  when the passport number acquired by the second acquirer matches the passport number acquired by the first acquirer from the person presumed as the suspicious person, the monitoring unit determines that the person presumed as the suspicious person enters the third region.

With the item 3, the passport number is acquired in addition to the first image data of the suspicious person in the first region. Therefore, it is possible to surely find out the suspicious person in the third region by checking the passport number acquired in the third region with the passport number of the person presumed as the suspicious person. It is possible to track an action of the suspicious person in the second region using the first image data concerning the person presumed as the suspicious person.

[Item 4]
The suspicious person report system according to the item 1, further including a third camera that acquires third image data including an image of the person in the third region, wherein when detecting, in the second image data, a person approaching the person presumed as the suspicious person within a first distance, the monitoring unit presumes that the approaching person is a related suspicious person, checks the third image data with the second image data including an image of the person presumed as the related suspicious person and determines that the person presumed as the related suspicious person enters the third region when the third image data includes an image of the person presumed as the related suspicious person, and when the monitoring unit determines that the person presumed as the related suspicious person enters the third region, the warning unit emits a warning.

With the configuration of the item 4, when a person entering an area within a predetermined first distance from the suspicious person is detected using the second image data, the person is presumed as a related suspicious person. Therefore, even if a suspicious object carried by the suspicious person is handed to the related suspicious person in the second region, it is possible to find out the related suspicious person and seize the suspicious object.

[Item 5]

The suspicious person report system according to the item 1, further including a third camera that acquires third image data including an image of the person in the third region, wherein when detecting, in the second image data, that a different person approaching the person presumed as the suspicious person within a first distance performs a specific action, the monitoring unit presumes that the dofferent person performing the specific action is a related suspicious person, checks the third image data with the second image data including an image of the different person presumed as the related suspicious person and determines that the different person presumed as the related suspicious person enters the third region when the third image data includes an image of the different person presumed as the related suspicious person, and when the monitoring unit determines that the person presumed as the related suspicious person enters the third region, the warning unit emits a warning.

With the configuration of the item 5, when it is detected from the second image data that a person entering an area within a predetermined first distance from the suspicious person performs the specific action, the person is presumed as a related suspicious person. Therefore, even if a suspicious object carried by the suspicious person is handed to the related suspicious person in the second region, it is possible to find out the related suspicious person and seize the suspicious object.

[Item 6]

The suspicious person report system according to the item 1, further including a third camera that acquires third image data including an image of the person in the third region, wherein when detecting, in the second image data, that any of belongings of the person presumed as the suspicious person is handed to a different person, the monitoring unit presumes that the different person is a related suspicious person, checks the third image data with the second image data including an image of the different person presumed as the related suspicious person and, when the third image data includes an image of the different person presumed as the related suspicious person, determines that the different person presumed as the related suspicious person enters the third region, and when the monitoring unit determines that the person presumed as the related suspicious person enters the third region, the warning unit emits a warning.

With the configuration of the item 6, when it is detected using the second image data that any of belongings of the suspicious person is handed to a different person, the different person is presumed as a related suspicious person. Therefore, even if a suspicious object, which is any of belongings of the suspicious person, is handed to the related suspicious person in the second region, it is possible to find out the related suspicious person and seize the suspicious object.

[Item 7]

The suspicious person report system according to the item 1, wherein the first image data includes a face image of the person; and the warning unit displays the face image of the person presumed as the suspicious person.

With the configuration of the item 7, since a report of the suspicious person is performed by displaying the face image of the suspicious person on a display device, it is easy to find out the suspicious person.

[Item 8]

The suspicious person report system according to the item 1, further including a memory that records the first image data corresponding to the person presumed as the suspicious person, wherein the monitoring unit checks the second image data with the first image data recorded in the memory to thereby track the person presumed as the suspicious person in the second region.

[Item 9]

The suspicious person report system according to the item 2, further including a memory that records the first image data corresponding to the person presumed as the suspicious person, wherein the monitoring unit checks the third image data with the first image data recorded in the memory and determines that the person presumed as the suspicious person enters the third region when the third image data includes an image of the person presumed as the suspicious person.

[Item 10]

The suspicious person report system according to the item 3, further including a memory that records the passport number corresponding to the person presumed as the suspicious person, the passport number being acquired by the first acquirer, wherein when the passport number acquired by the second acquirer matches the passport number recorded in the memory, the monitoring unit determines that the person presumed as the suspicious person enters the third region.

[Item 11]

The suspicious person report system according to any one of the items 1 to 10, wherein the first region is an immigration check area, and the third region is a customs area.

With the configuration of the item 11, it is possible to emit the warning when the person presumed as the suspicious person in the immigration check area enters the customs area.

[Item 12]

The suspicious person report system according to the item 11, wherein the warning unit emits the warning to an officer in the customs area.

With the configuration of the item 12, since the warning is emitted to the officer in the customs, it is possible to surely prevent entrance of the suspicious person into a country.

[Item 13]

A suspicious person report system, comprising:
a biometric sensor that detects biometric data of a person in a first region;
a presuming unit that calculates, from the biometric data, a stress index indicating a degree of stress and presumes that the person is a suspicious person when the calculated stress index is higher than a predetermined reference value;
a first acquirer that acquires first identification information of the person in the first region;
a second acquirer that acquires second identification information of the person entering a second region where the person proceeds after leaving the first region;
a monitoring unit that determines whether or not the second identification information matches the first identification information corresponding to the person presumed as the suspicious person; and
a warning unit that emits a warning when the monitoring unit determines that the second identification information matches the first identification information corresponding to the person presumed as the suspicious person.

With the configuration of the item 13, the biometric data of the person entering the first region is acquired. If the stress index obtained from the biometric data is higher than the reference value, the person is presumed as a suspicious person. The first identification information of the person is acquired.

In the second region where the person proceeds after leaving the first region, the second identification information of the person entering the second region is acquired.

When the first identification information of the person presumed as the suspicious person, and the second identification information match each other, the warning is emitted.

Therefore, even if an officer permits passage of the suspicious person in the first region, since the warning is emitted when the suspicious person enters the second region, it is possible to find out the suspicious person.

In this way, according to this aspect, it is possible to find out a suspicious person by effectively using two or more regions located apart from one another where an entrant is obliged to pass in order.

[Item 14]

The suspicious person report system according to the item 13, wherein
the first identification information includes first image data including an image of the person,
the second identification information includes second image data including an image of the person, and
the monitoring unit checks the second image data with the first image data corresponding to the person presumed as the suspicious person and determines that the second identification information matches the first identification information when the second image data includes an image of the person presumed as the suspicious person.

With the configuration of the item 14, the first image data of the suspicious person is acquired in the first region and, if the second image data acquired in the second region includes the image of the suspicious person, it is determined that the first identification information and the second identification information match each other, and the warning is emitted. Therefore, it is possible to find out the suspicious person using image data as identification information.

[Item 15]

The suspicious person report system according to the item 13, wherein
the first identification information includes a first passport number,
the second identification information includes a second passport number, and
the monitoring unit determines whether or not the second passport number matches the first passport number corresponding to the person presumed as the suspicious person.

With the configuration of the item 15, a first passport number of the suspicious person is acquired in the first region and the warning is emitted if the first passport number and a second passport number acquired in the second region match each other. Therefore, it is possible to find out the suspicious person by effectively using a passport number uniquely allocated to the person.

[Item 16]

The suspicious person report system according to the item 14, wherein
the first image data and the second image data each include an face image of the person, and
the warning unit displays the face image corresponding to the person presumed as the suspicious person.

With the configuration of the item 16, since the suspicious person is reported by displaying the face image of the suspicious person on a display device, it is easy to find out the suspicious person.

[Item 17]

The suspicious person report system according to the item 15, wherein
the first identification information further includes first image data including an image of the person, and
the warning unit displays the image of the person presumed as the suspicious person.

With the configuration of the item 17, since a report of the suspicious person is performed by displaying the face image of the suspicious person on a display device, it is easy to find out the suspicious person.

[Item 18]

The suspicious person report system according to the item 13, further including a memory that records the first identification information corresponding to the person presumed as the suspicious person, wherein
the monitoring unit determines whether or not the second identification information matches the first identification information recorded in the memory.

[Item 19]

The suspicious person report system according to any one of the items 13 to 18, wherein
the first region is an immigration check area, and
the second region is a customs area.

With the configuration of the item 19, it is possible to emit the warning when the person presumed as the suspicious person in the immigration check area enters the customs area.

[Item 20]

The suspicious person report system according to the item 19, wherein the warning unit emits the warning to an officer in the customs area.

With the configuration of the item 20, since the warning is emitted to the officer in the customs, it is possible to prevent entrance of the suspicious person into a country.

Embodiment

FIG. 1 is a schematic diagram of an airport to which a suspicious person report system 1 according to an embodiment of the present disclosure is applied. The airport is an international airport and includes an arrival gate G, an immigration check area A1, a customs area A3, and a passage A2 that connects the immigration check area A1 and the customs area A3. The immigration check area A1 is an example of a first region. The customs area A3 is an example of a third region. The passage A2 is an example of a second region. The arrival gate G is a place where an entrant 200 disembarking from an airplane F arriving from a foreign country passes first. The entrant 200 (an example of a person) passed through the arrival gate G advances to the immigration check area A1 first.

In the immigration check area A1, an immigration check of the entrant 200 is performed. In the immigration check area A1, there is one or more immigration check gates G1 where one or more immigration officers 100 are posted. The immigration officer 100 checks a passport of the entrant 200 and questions about a purpose of entry and the like to check whether the entrant 200 is a suspicious person. When determining that the entrant 200 is not a suspicious person, the immigration officer 100 permits the entrant 200 to pass the immigration check gate G1. On the other hand, when determining that the entrant 200 is a suspicious person, the immigration officer 100 does not permit the entrant 200 to pass the immigration check gate G1.

The entrant 200 permitted to pass the immigration check gate G1 moves to the customs area A3 through the passage A2. In the customs area A3, it is inspected whether the entrant 200 intends to smuggle articles prohibited to be brought into the country.

In the customs area A3, there are one or more customs gates G2 where one or more customs officers 400 are posted. The customs officer 400 asks the entrant 200 various questions to determine whether the entrant 200 is a suspicious person. When determining that the entrant 200 is a suspicious person, the customs officer 400 checks belongings of the entrant 200. When determining that the entrant 200 is not a suspicious person, the customs officer 400 permits the entrant 200 to pass the customs gate G2. When determining that the entrant 200 is a suspicious person, the customs officer 400 does not permit the entrant 200 to pass the customs gate G2.

In the immigration check area A1, one or more biometric sensors 2, one or more first cameras 3, and one or more first scanners 61 are disposed respectively at the one or more immigration check gates G1. One or more second cameras 4 are disposed in the passage A2. In the customs area A3, one or more third cameras 5, one or more second scanners 62, and one or more warning units 9 are disposed respectively at the one or more customs gates G2.

A monitoring unit 7 is communicatively connected to a presuming unit 6. The presuming unit 6 and the monitoring unit 7 are each configured by a computer. The presuming unit 6 is communicatively connected to the biometric sensor 2. The monitoring unit 7 is communicatively connected to the first camera 3, the first scanner 61, the second camera 4, the third camera 5, and the second scanner 62. In the example shown in FIG. 1, the presuming unit 6 and the monitoring unit 7 are configured by separate computers and communicatively connected to each other via a communication line such as a LAN. However, this is an example. The presuming unit 6 and the monitoring unit 7 may be configured by one computer. The presuming unit 6 and the monitoring unit 7 may be set in an airport or may be set outside the airport. The presuming unit 6 and the monitoring unit 7 may be a cloud server present on a cloud.

First Embodiment

Figure 2:
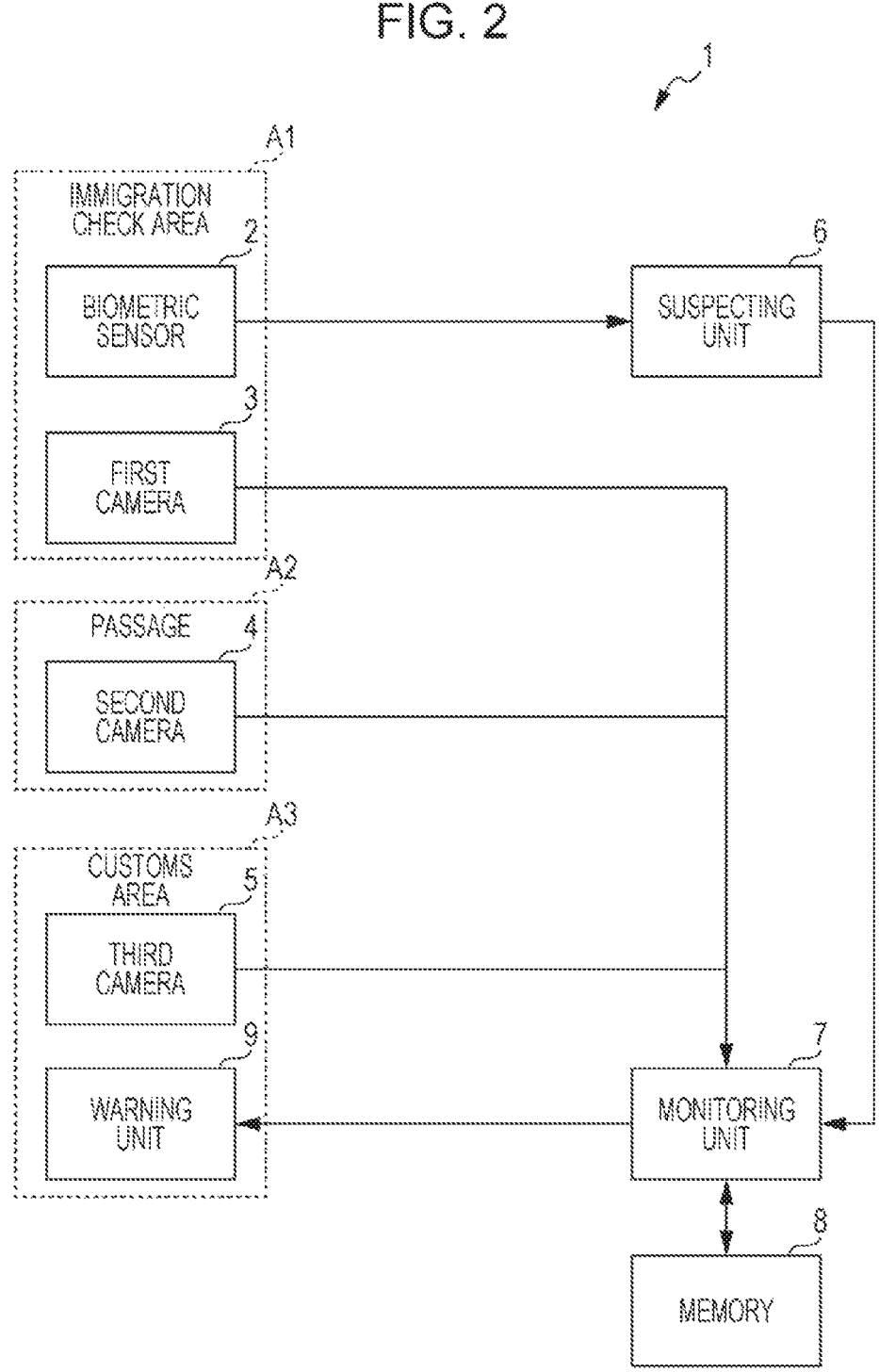
FIG. 2 is a block diagram showing an overall configuration of a suspicious person report system according to a first embodiment.

FIG. 2 is a block diagram showing an overall configuration of the suspicious person report system 1 according to a first embodiment. The suspicious person report system 1 includes the biometric sensor 2, the first camera 3, the second camera 4, the third camera 5, the presuming unit 6, the monitoring unit 7, a memory 8, and the warning unit 9. Note that, in the first embodiment, since the first scanner 61 and the second scanner 62 are not used, the first scanner 61 and the second scanner 62 are not shown in FIG. 2.

The biometric sensor 2 includes a measurer that measures biometric data, a processor that performs predetermined signal processing on measurement data measured by the measurer, and a communicator that transmits the biometric data to the presuming unit 6. The predetermined signal processing is, for example, noise removal processing. The biometric sensor 2 detects biometric data of a person who enters the immigration check area A1. As the biometric data, for example, vital data such as a brain wave, a brain blood flow, a pulse wave, a blood pressure, a respiration rate, a body temperature, and perspiration can be adopted.

When the brain wave and the brain blood flow are adopted as the biometric data, a brain wave meter and a brain blood flow meter can be adopted as the biometric sensor 2. When the pulse wave and the blood pressure are adopted as the biometric data, a brain wave meter and a blood pressure meter can be adopted as the biometric sensor 2. When the respiration rate is adopted as the biometric data, a respiration meter can be adopted as the biometric sensor 2. When the body temperature is adopted as the biometric data, a thermometer can be adopted as the biometric sensor 2. When the perspiration is adopted as the biometric data, a perspiration state meter can be adopted as the biometric sensor 2. When a thermal image is adopted as the biometric data, an infrared camera can be adopted as the biometric sensor 2. The biometric sensor 2 may be a biometric sensor that detects biometric data in non-contact with a person or may be a biometric sensor that detects biometric data in contact with the person.

The biometric sensor 2 is communicatively connected to the presuming unit 6 by radio or wire. Under an instruction of the immigration officer 100, when measurement of biometric data is started, the biometric sensor 2 only has to measure biometric data at a fixed sampling interval and transmit a measurement value to the presuming unit 6 in association with a user ID. The user ID is a symbol string uniquely given to identify an individual entrant 200.

As the radio, a wireless LAN such as Bluetooth (registered trademark) or IEEE802.11 can be adopted. As the wire, Ethernet (registered trademark) can be adopted.

The presuming unit 6 calculates, from the biometric data detected by the biometric sensor 2, a stress index indicating a degree of stress of the entrant 200 and, when the stress index is higher than a predetermined reference value, presumes the entrant 200 as a suspicious person, and transmits a detection signal indicating that the suspicious person is detected to the monitoring unit 7. The detection signal includes a user ID given to the biometric data of the suspicious person.

For example, Japanese Patent No. 5257525 (JP5257525B) discloses a technique for performing a frequency analysis of fluctuation in a heartbeat interval from brain wave data to detect stress of a person. Specifically, it is disclosed that the frequency analysis of the heartbeat interval is performed to detect a level HF of a high-frequency peak that occurs at a frequency of about 0.3 Hz and a level LF of a low-frequency peak that occurs at a frequency of about 0.1 Hz and determine that stress of a person is higher as LF/HF is larger.

Therefore, the presuming unit 6 only has to adopt the LF/HF disclosed in the patent as a stress index of the entrant 200 and, when the stress index is larger than a predetermined threshold, determine the entrant 200 as a suspicious person.

Japanese Patent No. 5735592 (JP5735592B) discloses that a comfortableness degree of a user is evaluated in ten stages of −5 to +5 from biometric data such as a heart rate, a pulse, and a body temperature.

Therefore, the presuming unit 6 only has to adopt the comfortableness degree disclosed in the patent as a stress index and, when the stress index is larger than a threshold, determine the entrant 200 as a suspicious person. In this case, the presuming unit 6 only has to calculate the stress index from a brain wave, a brain blood flow, a pulse, a blood pressure, a respiration rate, a body temperature, and perspiration.

Japanese Unexamined Patent Application Publication No. 2012-249797 (JP2012-249797A) discloses that a value obtained by linearly combining a heart rate, a body temperature, a blood pressure, and perspiration is calculated as a stress value.

Therefore, the presuming unit 6 only has to adopt the stress value disclosed in the publication as a stress index and, when the stress index is larger than a threshold, determine that the entrant 200 is a suspicious person.

The presuming unit 6 may calculate a stress index of the entrant 200 from thermal image data as disclosed in P2003-534864A.

The first camera 3 is provided in the immigration check area A1, captures an image of each entrant 200 entering a predetermined check position before the immigration check gate G1, and acquires first image data including an image of the entrant 200. An optical axis and an angle of view of the first camera 3 are set such that the first camera 3 can capture an image of the face or the whole body of the entrant 200 entering the check position. Every time a new entrant 200 enters the check position of the immigration check gate G1, the first camera 3 captures an image of the entrant 200 and outputs obtained first image data to the monitoring unit 7.

The second camera 4 is provided in the passage A2, captures an image of a person passing the passage A2 at a predetermined frame rate, and transmits a captured image to the monitoring unit 7. When the total length of the passage A2 is long and one second camera 4 cannot capture an image of the entire region of the passage A2, two or more second cameras 4 may be set such that the entire region of the passage A2 can be captured.

The third camera 5 is provided in the customs area A3, captures an image of each entrant 200 entering a predetermined check position before the customs gate G2, and acquires third image data including an image of the entrant 200. An optical axis and an angle of view of the third camera 5 are set such that the third camera 5 can capture an image of the face or the whole body of the entrant 200 entering the check position. Every time a new entrant 200 enters the check position of the customs gate G2, the third camera 5 captures an image of the entrant 200 and outputs obtained third image data to the monitoring unit 7.

The monitoring unit 7 records the first image data of the suspicious person presumed by the presuming unit 6 in the memory 8 and checks the second image acquired by the second camera 4 with the first image data recorded in the memory 8 to thereby track the suspicious person in the passage A2.

Specifically, when receiving the detection signal transmitted from the presuming unit 6, the monitoring unit 7 records the first image data captured by the first camera 3 in a suspicious person management table T1 included in the memory 8 in association with a user ID included in the detection signal.

Figures 3, 4:
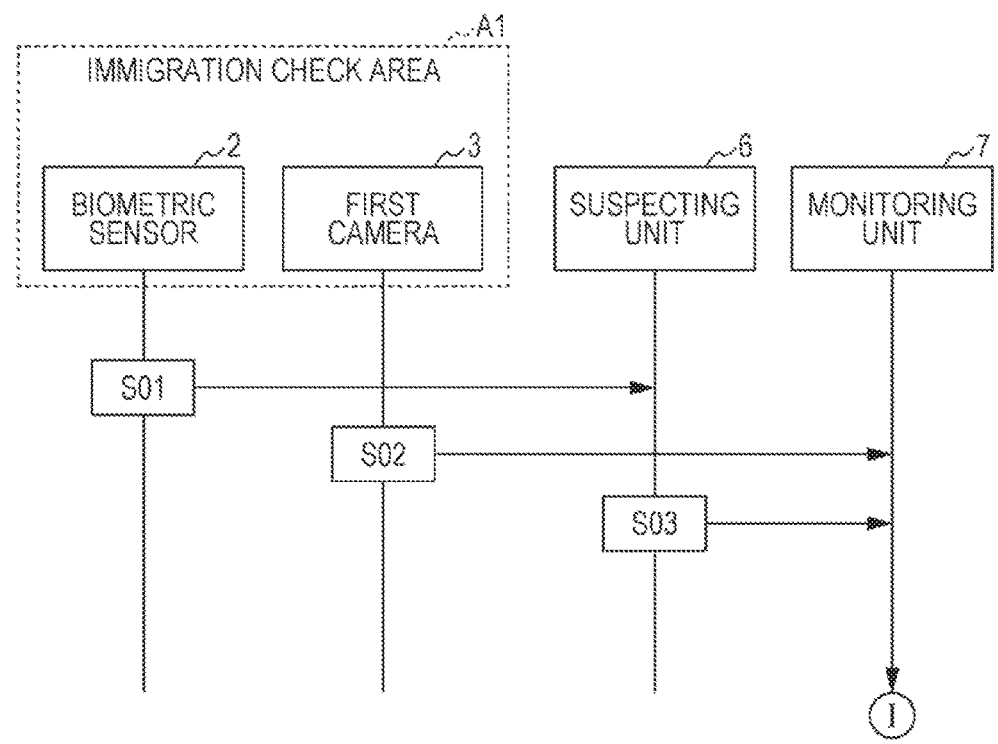
FIG. 3 is a diagram showing an example of a suspicious person management table according to the first embodiment.
FIG. 4 is a sequence chart showing the operation of the suspicious person report system.

FIG. 3 is a diagram showing an example of the suspicious person management table T1 according to the first embodiment. The suspicious person management table T1 is a two-dimensional table in which user IDs and image data are recorded in association with each other. A user ID issued by the monitoring unit 7 is recorded in a field of "user ID". First image data concerning the user ID is recorded in a field of "image data".

The monitoring unit 7 checks the second image data captured by the second camera 4 with the first image data recorded in the suspicious person management table T1 to track a suspicious person passing the passage A2. The monitoring unit 7 calculates similarity of a feature value of the suspicious person extracted from the first image data and feature values of one or more objects included in the second image data and, if an object having similarity equal to or larger than a specified value is included in the second image data, determines that the suspicious person is included in the second image data. The monitoring unit 7 tracks the suspicious person by marking, in the second image data, the object indicating the suspicious person to track the suspicious person until the suspicious person frames out from an exit of the passage A2.

As the feature value of the suspicious person, a feature value of the face of the suspicious person may be adopted or a feature value of clothes worn by the suspicious person may be adopted. The monitoring unit 7 records the first image data of the suspicious person in the suspicious person management table T1. However, this is an example. The monitoring unit 7 may record a feature value of the suspicious person extracted from the first image data. The same applies to embodiments explained below.

Referring back to FIG. 2, every time the third image data is transmitted from the third camera 5, the monitoring unit 7 checks the third image data with the first image data recorded in the suspicious person management table T1 and determines whether the suspicious person is included in the third image data. When the suspicious person is included in the third image data, the monitoring unit 7 determines that the suspicious person enters the customs area A3. Specifically, the monitoring unit 7 calculates similarity of a feature value of the suspicious person extracted from the first image data and a feature value of a person extracted from the third image data and, if the calculated similarity is equal to or larger than a specified value, determines that the suspicious person enters the customs area A3. As the specified value, a predetermined value for regarding two of them as the same person can be adopted.

When determining that the suspicious person enters the customs area A3, the monitoring unit 7 causes the warning unit 9 to emit a warning.

The warning unit 9 is configured by a display device set in the customs area A3. As the display device, a liquid crystal display, an organic EL display, and the like can be adopted. A display surface of the display device faces the customs officer 400. The display device is disposed such that only the customs officer 400 can visually recognize an image.

The warning unit 9 only has to emit a warning by, for example, displaying a face image of the suspicious person or a whole body image of the suspicious person. In this case, the warning unit 9 only has to receive image data of the suspicious person from the monitoring unit 7 and display the image of the suspicious person. As a warning method by the warning unit 9, an aspect in which the face image and the whole body image are displayed on the display device is explained above. However, this is an example. For example, the warning unit 9 may be configured by an LED lamp and turn on the LED lamp to emit a warning. Alternatively, the warning unit 9 may be configured by a speaker and emit a warning by outputting, from the speaker, a voice message for informing that the suspicious person enters the customs area A3.

The memory 8 is configured by a nonvolatile rewritable storage device mounted on a computer communicatively connected to the monitoring unit 7 and stores the suspicious person management table T1 and the like. The memory 8 may be connected to the monitoring unit 7 via a communication line such as a LAN or may be provided on the cloud. The memory 8 may be communicatively connected to the presuming unit 6. The memory 8 may be configured by the storage device of the monitoring unit 7.

<Sequence>

Figure 5:
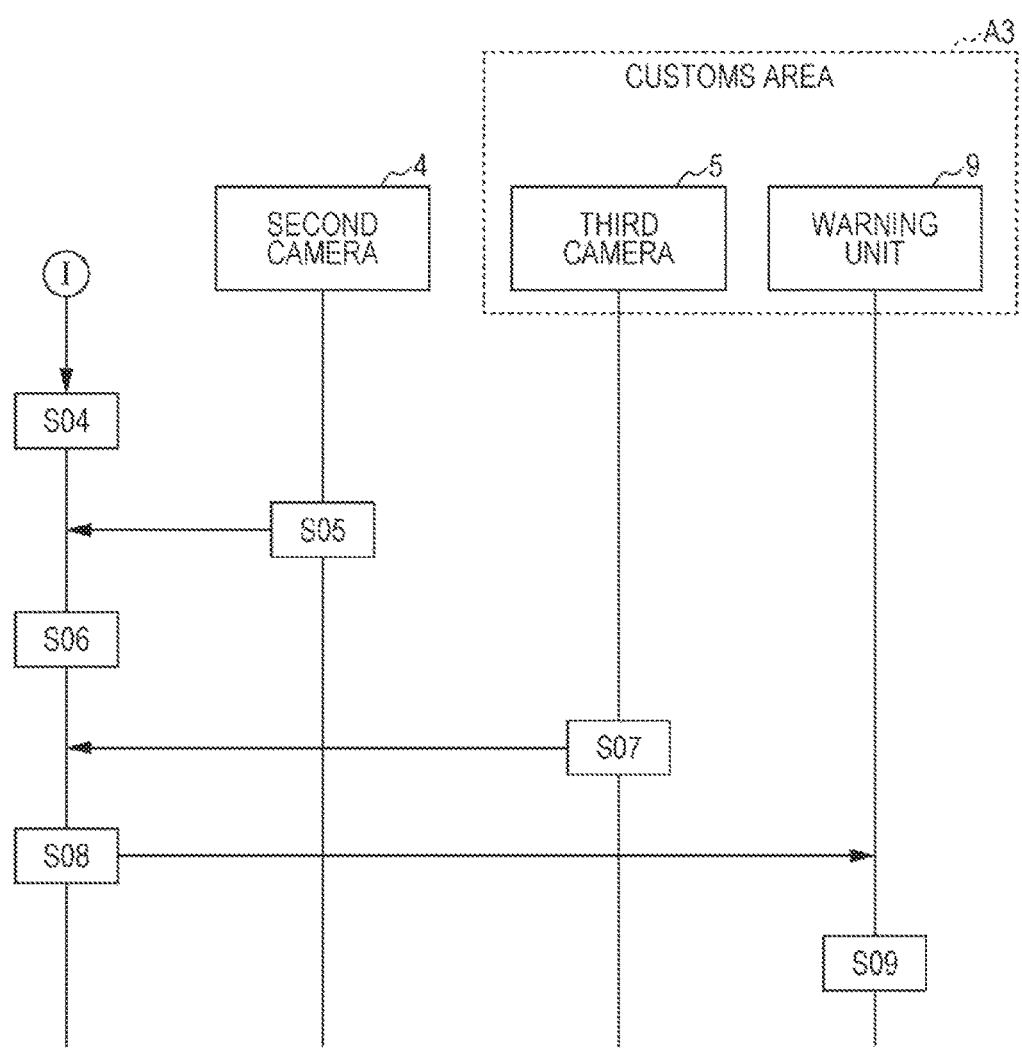
FIG. 5 is a sequence chart following FIG. 4.

The operation of the suspicious person report system 1 is explained. FIG. 4 is a sequence chart showing the operation of the suspicious person report system 1. FIG. 5 is a sequence chart following FIG. 4.

(S01) The biometric sensor 2 measures biometric data of the entrant 200 entering the check position in the immigration check area A1. The biometric sensor 2 gives a user ID to each entrant 200 and transmits the user ID to the presuming unit 6 in association with biometric data. Note that, when the biometric sensor 2 is configured by a contact-type biometric sensor, the biometric sensor 2 is attached to the entrant 200 by the immigration officer 100 or another officer. The biometric sensor 2 only has to start measurement of biometric data, for example, with an input of a measurement start instruction from the immigration officer 100 as a trigger, measure biometric data at a fixed sampling interval until a measurement end instruction is input from the immigration officer 100, and transmit the measured biometric data to the presuming unit 6 in association with a user ID.

(S02) In parallel to the processing in S01, the first camera 3 captures an image of the entrant 200 being checked, acquires first image data, and transmits the first image data to the monitoring unit 7. The first camera 3 only has to capture an image of an entrant, for example, with an input of an image capture instruction from the immigration officer 100 as a trigger and transmit the acquired first image data to the monitoring unit 7.

(S03) The presuming unit 6 calculates a stress index from the biometric data received from the biometric sensor 2 and determines whether the entrant 200 is a suspicious person. When determining that the entrant 200 is a suspicious person, the presuming unit 6 generates a detection signal including a user ID associated with biometric data of the suspicious person and transmits the detection signal to the monitoring unit 7. On the other hand, when determining that the entrant 200 is not a suspicious person, the presuming unit 6 ends the processing.

(S04) When receiving the detection signal, the monitoring unit 7 records the first image data transmitted from the first camera 3 in the suspicious person management table T1 in association with the user ID of the suspicious person included in the detection signal, Consequently, the first image data of the suspicious person is recorded. The monitoring unit 7 only has to record first image data transmitted within a fixed period around a time of reception of the detection signal in the suspicious person management table T1 as the first image data of the suspicious person. As the fixed period, a period estimated to be consumed for measurement of biometric data and capturing of first image data concerning the same person is adopted.

(S05) The second camera 4 transmits the second image data to the monitoring unit 7. Note that the second camera 4 always captures an image of the passage A2 at a predetermined frame rate and transmits the second image data to the monitoring unit 7 at the predetermined frame rate.

(S06) The monitoring unit 7 checks the second image data captured by the second camera 4 with the first image data of the suspicious person recorded in the suspicious person management table T1 and determines whether the suspicious person is included in the second image data. When the suspicious person is included in the second image data, the monitoring unit 7 marks the suspicious person in the second image data and tracks the suspicious person until the suspicious person frames out from the exist of the passage A2, When the suspicious person is not included in the second image data, the monitoring unit 7 ends the processing.

(S07) The third camera 5 captures an image of the entrant 200 entering the check position in the customs area A3, acquires third image data of the entrant 200, and transmits the third image data to the monitoring unit 7. The third camera 5 only has to capture an image of the entrant 200, for example, with an input of an image capture instruction from the customs officer 400 as a trigger and transmit the third image data to the monitoring unit 7.

(S08) The monitoring unit 7 checks the third image data captured by the third camera 5 with the first image data of the suspicious person recorded in the suspicious person management table T1 and determines whether the suspicious person is included in the third image data.

(S09) When the monitoring unit 7 determines that the suspicious person is included in the third image data, the warning unit 9 displays a face image or a whole body image of the suspicious person on the display device. Consequently, the customs officer 400 can recognize that the entrant 200 in front of the customs officer 400 is the suspicious person and can take necessary measures. Examples of the necessary measures include a measure for opening a bag carried by the suspicious person and inspecting belongings of the suspicious person in detail and a measure for moving the suspicious person to another interrogation room and interrogating the suspicious person.

As explained above, with the suspicious person report system 1, the biometric data and the first image data of the entrant 200 entering the immigration check area A1 are acquired and, if the stress index obtained from the biometric data is higher than the reference value, the entrant 200 is presumed as a suspicious person, and the first image data is recorded in the memory 8.

An action of the suspicious person is monitored in the passage A2 by checking the second image data captured by the second camera 4 with the first image data recorded in the memory 8.

When the suspicious person indicated by the first image data recorded in the memory 8 is included in the third image data obtained by capturing an image of the entrant 200 entering the customs area A3 with the third camera 5, the warning is emitted.

Therefore, even if the immigration officer 100 permits passage of the suspicious person in the immigration check area A1, since the warning is emitted when the suspicious person enters the customs area A3, it is possible to find out the suspicious person. In this way, the suspicious person report system 1 can find out the suspicious person by effectively using the immigration check area A1 and the customs area A3 provided apart from each other where an entrant is obliged to pass in order in the airport.

Since an action of the suspicious person is monitored in the passage A2 as well, even if the suspicious person performs an action for handing a suspicious object carried by the suspicious person to a different person in the passage A2, it is possible to find out the fact by analyzing the second image data.

Note that, since the passage A2 and the customs area A3 are continuous, the second camera 4 is sometimes capable of tracking an entrant to find which customs gate G2 the entrant enters. In an airport where there is only one customs gate G2, the entrant 200 framing out from the exit of the passage A2 can be regarded as entering the customs gate G2 next.

Therefore, if the customs gate G2 that the suspicious person enters can be found out using the second image data, the monitoring unit 7 may cause the warning unit 9 of the customs gate G2 to emit a warning. Alternatively, in the airport where there is only one customs gate G2, when the monitoring unit 7 can confirm that the suspicious person frames out from the exit of the passage A2 in the second image data, the monitoring unit 7 may cause the warning unit 9 to emit a warning. In this case, the monitoring unit 7 can emit the warning without using the third camera 5. Therefore, the third camera 5 is unnecessary.

Second Embodiment

Figure 6:
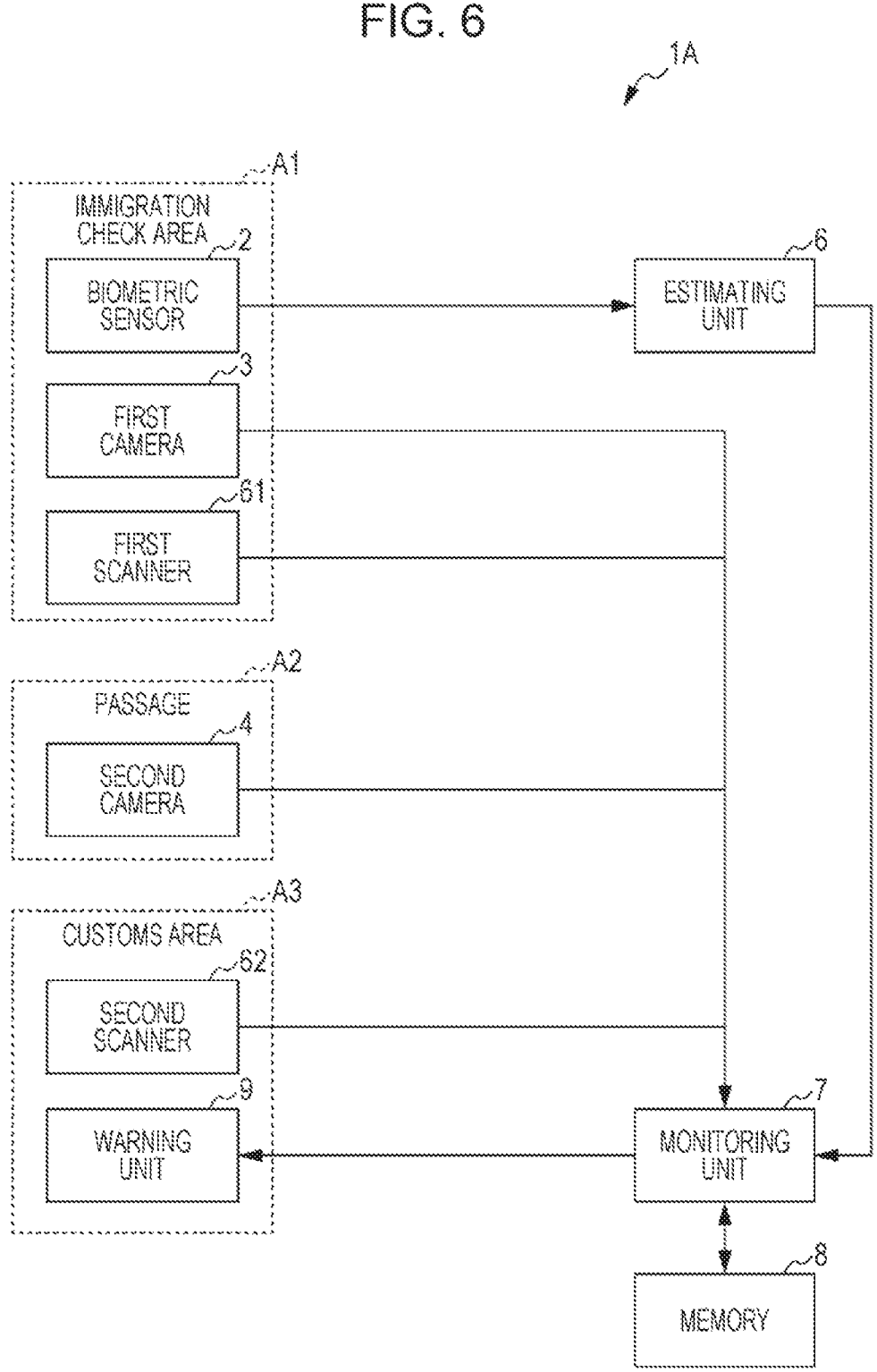
FIG. 6 is a block diagram showing an overall configuration of a suspicious person report system according to a second embodiment.

FIG. 6 is a block diagram showing an overall configuration of a suspicious person report system 1A according to a second embodiment. The suspicious person report system 1A is characterized by reporting a suspicious person using a passport number of a passport carried by the entrant 200. FIG. 6 is different from FIG. 2 in that a first scanner 61 is added in the immigration check area A1 and a second scanner 62 is provided instead of the third camera 5 in the customs area A3. Note that, in the second embodiment, components same as the components in the first embodiment are denoted by the same reference numerals and signs and explanation of the components is omitted.

The first scanner 61 is provided in the immigration check area A1, reads, according to an instruction of the immigration officer 100, a passport number described in a passport presented by the entrant 200 in the immigration check gate G1, and transmits the passport number to the monitoring unit 7. Note that, in the case of a passport in which a passport number is stored in an electronic chip, the first scanner 61 only has to acquire the passport number by communicating with the electronic chip. The same applies to the second scanner 62.

The second scanner 62 is provided in the customs area A3, reads, according to an instruction of the customs officer 400, a passport number described in a passport presented by the entrant 200 in the customs gate G2, and transmits the passport number to the monitoring unit 7.

When receiving a detection signal from the presuming unit 6, the monitoring unit 7 records the first image data transmitted from the first camera 3 and the passport number transmitted from the first scanner 61 in the same period in a suspicious person management table T2 (FIG. 7) included in the memory 8 in association with each other.

When the passport number of the suspicious person recorded in the suspicious person management table T2 and the passport number read by the second scanner 62 match each other, the monitoring unit 7 causes the warning unit 9 to emit a warning.

Figures 7, 8:
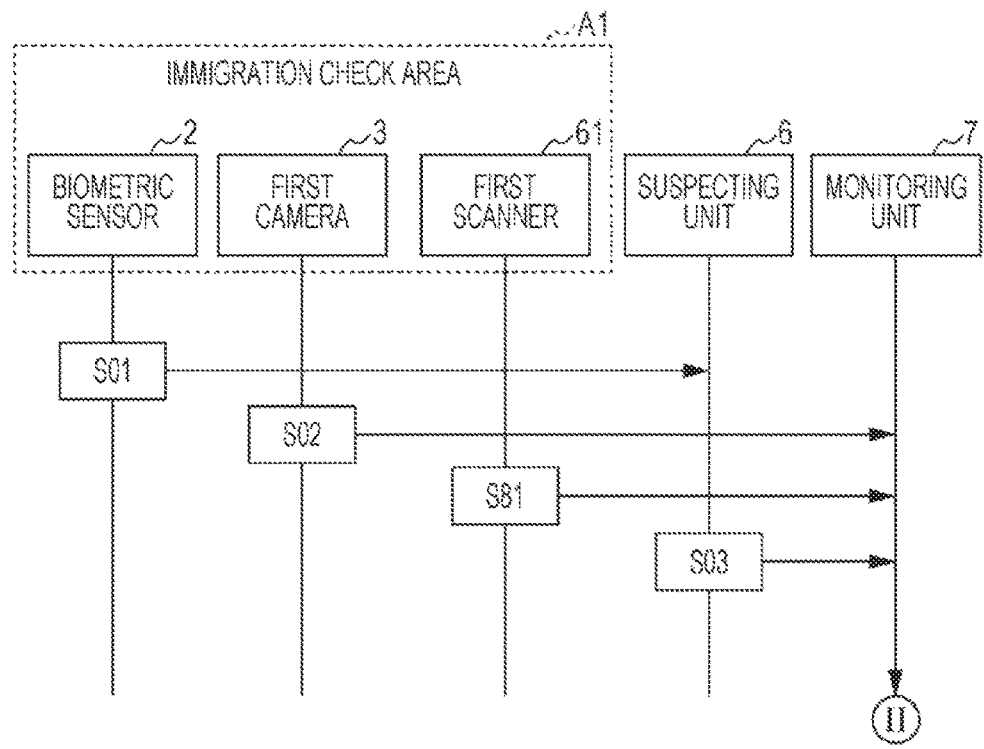
FIG. 7 is a diagram showing an example of a suspicious person management table according to the second embodiment.
FIG. 8 is a sequence chart showing the operation of the suspicious person report system according to the second embodiment.

FIG. 7 is a diagram showing an example of the suspicious person management table T2 according to the second embodiment. The suspicious person management table T2 is different from the suspicious person management table T1 in that a passport number is provided instead of the user ID. Since the passport number is uniquely given to the individual entrant 200, the passport number is capable of uniquely identifying a suspicious person. Therefore, in the second embodiment, the passport number is adopted instead of the user ID, Note that, in the second embodiment, image data of a suspicious person is recorded in the suspicious person management table T2 in order to track the suspicious person in the second image data.

In the second embodiment, since a user ID is not used, the biometric sensor 2 does not need to issue a user ID. Therefore, it is possible to reduce a processing load on the biometric sensor 2.

<Sequence>

Figure 9:
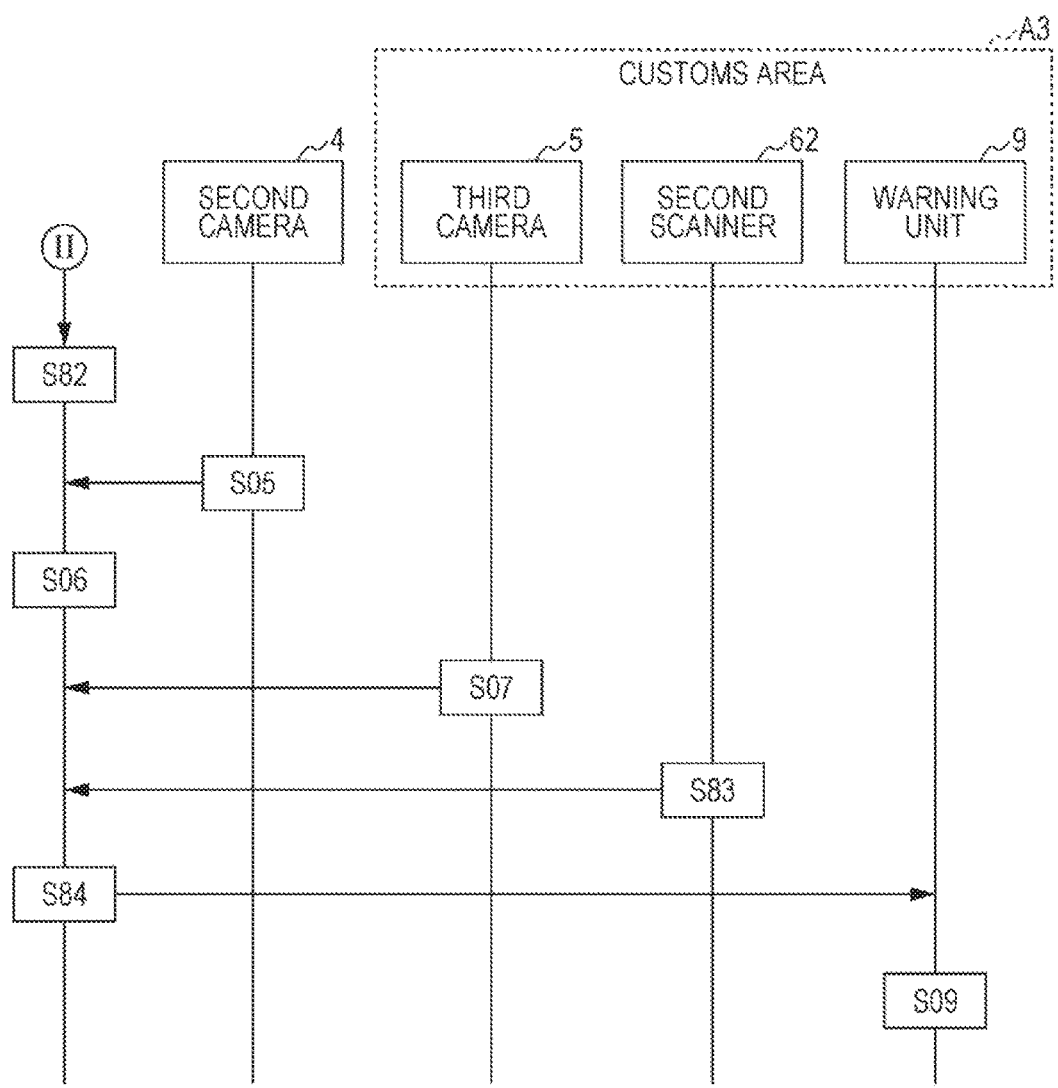
FIG. 9 is a sequence chart following FIG. 8.

FIG. 8 is a sequence chart showing the operation of the suspicious person report system 1A according to the second embodiment. FIG. 9 is a sequence chart following FIG. 8.

Note that, in FIGS. 8 and 9, kinds of processing same as the kinds of processing shown in FIGS. 4 and 5 are denoted by the same reference signs and explanation of the kinds of processing is omitted.

(S81) S81 is processing performed in parallel to S01 and S02. The first scanner 61 reads a passport number of the entrant 200 and transmits the passport number to the monitoring unit 7.

(S82) S82 is processing following 303. When receiving a detection signal, the monitoring unit 7 records the first image data transmitted from the first camera 3 in the suspicious person management table T2 in association with the passport number transmitted from the first scanner 61. Consequently, the first image and the passport number of the suspicious person are recorded together. The monitoring unit 7 only has to record first image data and a passport number transmitted within a fixed period around a time of reception of the detection signal in the suspicious person management table T2 as the first image data and the passport number of the suspicious person. As the fixed period, a period estimated to be consumed for measurement of biometric data, capturing of first image data, and acquisition of a passport number of the same person is adopted.

(S83) S83 is processing following S07. The second scanner 62 reads, according to an instruction of the customs officer 400, a passport number presented by the entrant 200 entering the check position in the customs area A3 and transmits the passport number to the monitoring unit 7.

(S84) S84 is processing following S83. The monitoring unit 7 checks whether the passport number of the suspicious person recorded in the suspicious person management table T2 and the passport number read by the second scanner 62 match each other.

When the monitoring unit 7 determines that the two passport numbers match each other, the warning unit 9 emits a warning (S09). When the two passport numbers do not match each other, the processing ends.

As explained above, with the suspicious person report system 1A, the passport number is also acquired in addition to the first image data of the suspicious person in the immigration check area A1 and recorded in the suspicious person management table T2. Therefore, the suspicious person report system 1A can find out the suspicious person in the customs area A3 by checking the passport number acquired in the customs area A3 with the passport number recorded in the suspicious person management table T2. Since the first image data of the suspicious person is recorded in the suspicious person management table T2, the suspicious person report system 1A can track an action of the suspicious person in the passage A2 using the first image data.

Third Embodiment

Figure 10:
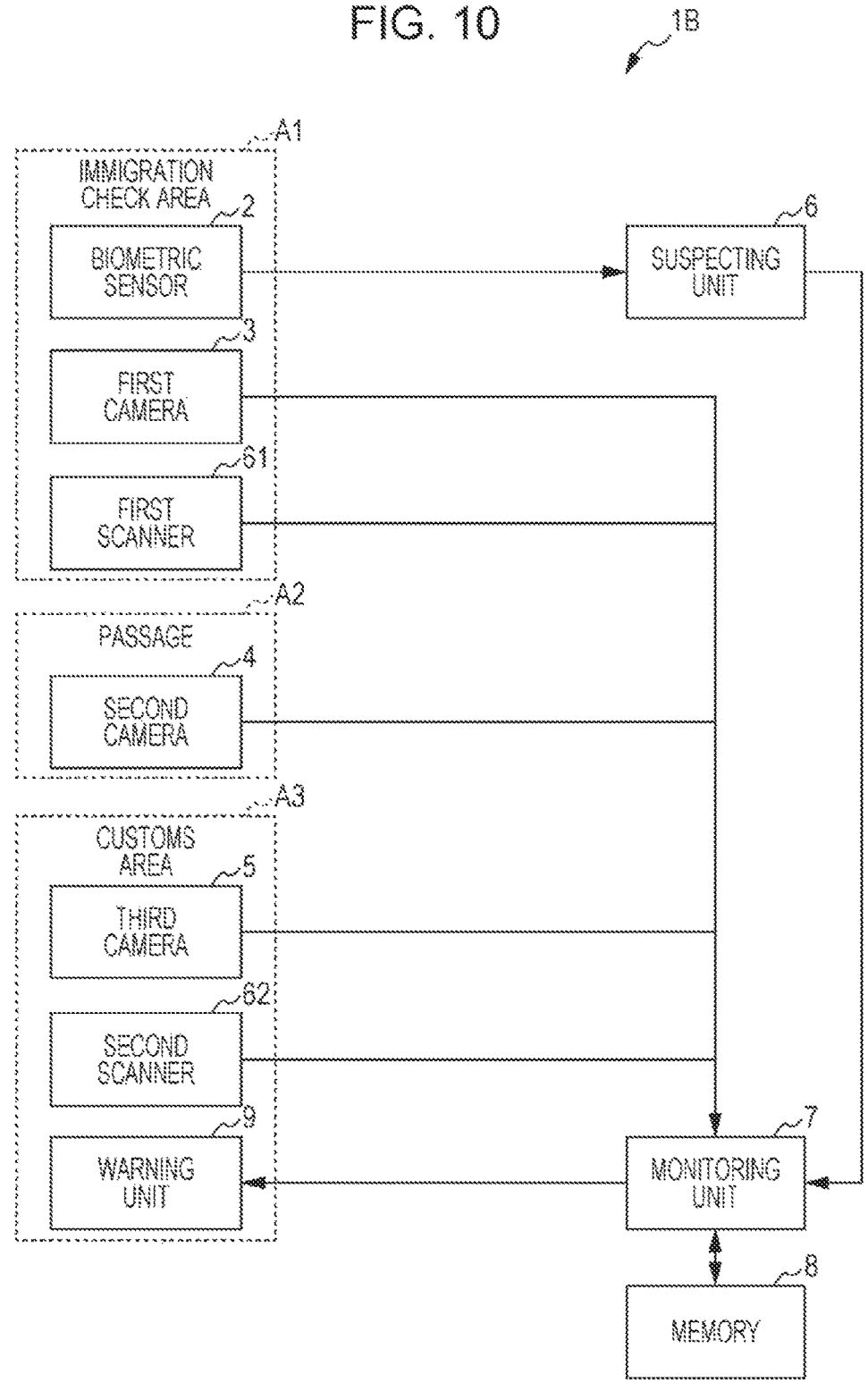
FIG. 10 is a block diagram showing an overall configuration of a suspicious person report system according to a third embodiment.

FIG. 10 is a block diagram showing an overall configuration of a suspicious person report system 1B according to a third embodiment. The suspicious person report system 1B is characterized by finding out, in the passage A2, a related suspicious person conspiring with a suspicious person. FIG. 10 is different from FIG. 6 in that the third camera 5 is provided in the customs area A3. Note that, in the third embodiment, components same as the components in the first and second embodiments are denoted by the same reference numerals and signs and explanation of the components is omitted.

When detecting, from second image data, that an entrant 200 different from a suspicious person being tracked in the second image data enters an area within a predetermined first distance from the suspicious person, the monitoring unit 7 presumes that the different entrant is a related suspicious person. The monitoring unit 7 extracts fourth image data indicating the presumed related suspicious person from the second image data and records the fourth image data in a suspicious person management table T3 included in the memory 8.

FIG. 11 is a diagram showing the suspicious person management table T3 according to the third embodiment. In the suspicious person management table T3, a field of "related suspicious person" is further provided in addition to the fields of the suspicious person management table T1 shown in FIG. 3. In the field of "related suspicious person", the fourth image data indicating the related suspicious person is recorded. As the fourth image data, a face image of the related suspicious person may be adopted or a whole body image of the related suspicious person may be adopted. As the fourth image data, a feature value of the face image of the related suspicious person or a feature value of the whole body image of the related suspicious person may be adopted.

Referring back to FIG. 10, the monitoring unit 7 checks the third image data captured by the third camera 5 with the fourth image data recorded in the suspicious person management table T3 and determines whether the related suspicious person is included in the third image data. When determining that the related suspicious person is included in the third image data, the monitoring unit 7 causes the warning unit 9 to emit a warning. Note that the monitoring unit 7 performs, in parallel, the determination concerning whether the suspicious person is included in the third image data captured by the third camera 5 explained in the first embodiment.

Figure 12:
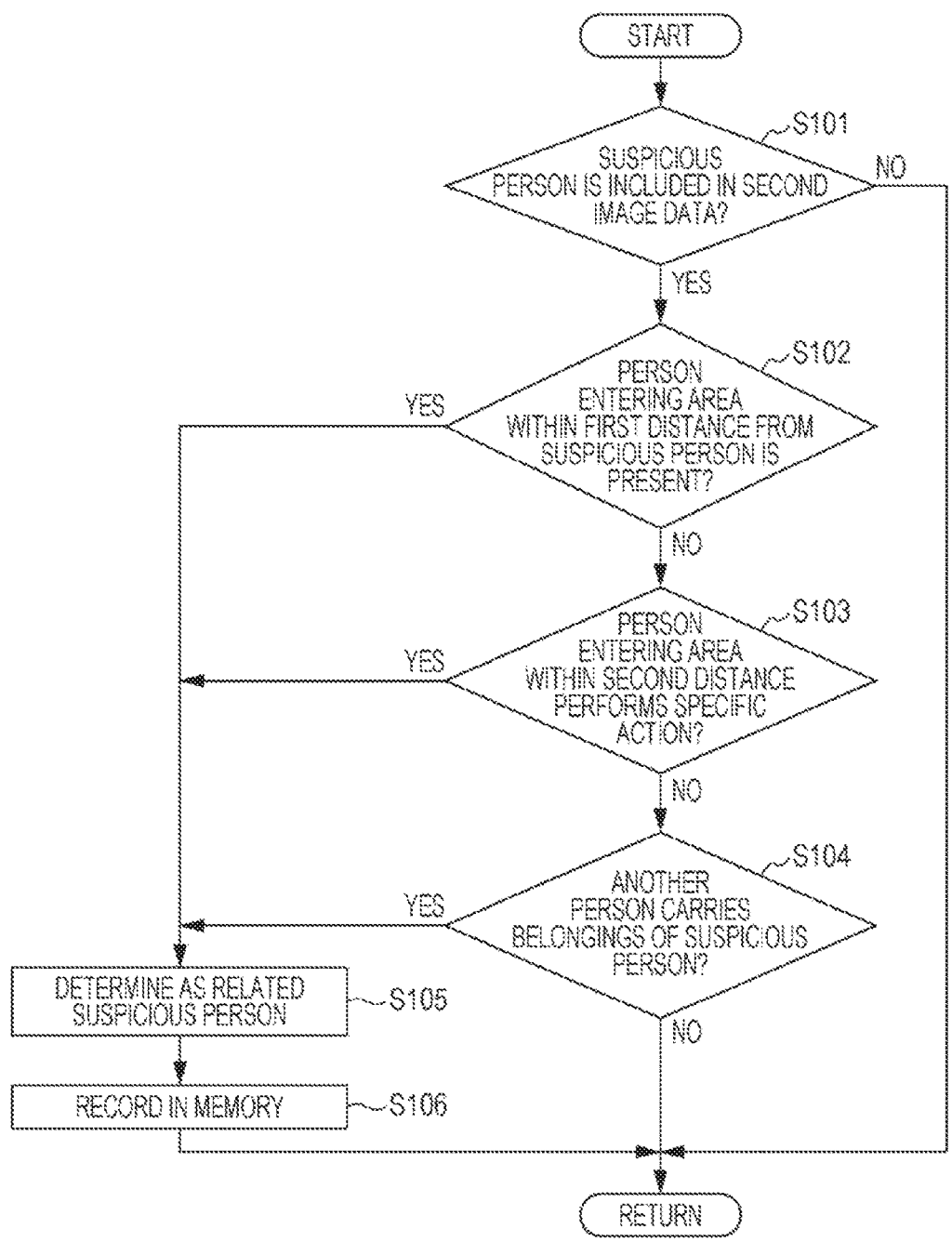
FIG. 12 is a flowchart for explaining processing for determining a related suspicious person.

FIG. 12 is a flowchart for explaining processing for determining a related suspicious person. In the third embodiment, the sequence chart in the first embodiment shown in FIGS. 4 and 5 is adopted as a sequence chart. The flowchart of FIG. 12 is executed in S06 shown in FIG. 5.

First, the monitoring unit 7 checks the second image data with the first image data recorded in the suspicious person management table T3 and determines whether the suspicious person is included in the second image data. If the suspicious person is included in the second image data (YES in S101), the monitoring unit 7 starts tracking of the suspicious person and determines, from the second image data, presence or absence of a person who enters within a first distance from the suspicious person being tracked (S102). On the other hand, if the suspicious person is not included in the second image data (NO in S101) the monitoring unit 7 ends the processing.

Examples of the first distance include an estimated distance between the suspicious person and a different person at which the suspicious person can take an action of handing any of belongings held by the suspicious person to a different person. Note that the monitoring unit 7 only has to execute processing in S102 by, for example, extracting, with image processing, movements of people appearing in the second image data including the suspicious person.

If there is a person entering the area within the first distance from the suspicious person (YES in S102), the monitoring unit 7 determines the person as a related suspicious person (S105). The monitoring unit 7 extracts the fourth image data indicating the related suspicious person from the second image data and records the fourth image data in the suspicious person management table T3 in association with a user ID of the suspicious person (S106).

On the other hand, if there is no person entering the area within the first distance from the suspicious person (NO in S102), the monitoring unit 7 advances the processing to S103.

In S103, the monitoring unit 7 determines whether a person entering an area within a second distance from the suspicious person performs a specific action. The second distance is larger than the first distance. As an example of the second distance, an estimated distance between the suspicious person and a different person at which the suspicious person can take an action of throwing any of belongings to the different person can be adopted.

Examples of the specific action include an action in which the person entering the area within the second distance receives the belonging from the suspicious person and an action in which the person entering within the second distance catches the belonging thrown by the suspicious person.

If the person entering the area within the second distance from the suspicious person performs the specific action (YES in S103), the processing proceeds to S105. If the person entering the area within the second distance from the suspicious person does not perform the specific action (NO in S103), the processing proceeds to S104.

In S104, the monitoring unit 7 determines whether the different person carries the belonging carried by the suspicious person. The monitoring unit 7 monitors the belongings of the suspicious person in the second image data. When detecting that any of the belongings is lost from the suspicious person and the different person carries the belonging, the monitoring unit 7 only has to determine that the different person carries the belonging carried by the suspicious person. Consequently, even if the second camera 4 cannot grasp a scene in which the suspicious person hands the belonging to the related suspicious person because the scene is hidden behind the different person or an obstacle, it is possible to detect the related suspicious person. Examples of the belongings of the suspicious person include a bag or a suitcase of the suspicious person and an article gripped by a hand of the suspicious person.

If the monitoring unit 7 detects in S104 that any of the belongings carried by the suspicious person is carried by the different person (YES in S104), the monitoring unit 7 advances the processing to S105. On the other hand, if the monitoring unit 7 does not detect that the belonging carried by the suspicious person is carried by the different person (NO in S104), the monitoring unit 7 ends the processing.

As explained above, with the suspicious person report system 1B, even if the suspicious person hands any of the belongings to a different person in the passage A2, the fourth image data indicating the different person is recorded in the suspicious person management table T3. When the related suspicious person is included in the third image data captured by the third camera 5, a warning is emitted. Therefore, it is possible to report presence of the related suspicious person conspiring with the suspicious person to the customs officer 400 in the customs area A3. As a result, it is possible to seize the belonging handed from the suspicious person to the related suspicious person as suspicious objects in the customs and find out the suspicious person and the related suspicious person.

Modification of the Third Embodiment

Note that, in the above explanation, the monitoring unit 7 checks the third image data with the first image data to determine whether the suspicious person is included in the third image data. However, this is an example. The monitoring unit 7 may find out the suspicious person using the method explained in the second embodiment.

In this case, the monitoring unit 7 only has to record the passport number read by the first scanner 61 in the suspicious person management table T4 in association with the first image data of the suspicious person. FIG. 13 is a diagram showing a suspicious person management table T4 according to a modification of the third embodiment. The suspicious person management table T4 includes a field of a passport number instead of the field of the user ID in the suspicious person management table T3.

When the passport number read by the second scanner 62 matches the passport number recorded in the suspicious person management table T4, the monitoring unit 7 determines that the suspicious person enters the customs area A3.

On the other hand, the related suspicious person indicated by the fourth image data is included in the third image data captured by the third camera 5, the monitoring unit 7 determines that the related suspicious person enters the customs area A3. The fourth image data is used concerning the related suspicious person rather than the passport number because, the passport number of the related suspicious person cannot be identified beforehand since the related suspicious person is detected when passing the passage A2.

As explained above, in the modification of the third embodiment, even when the suspicious person is found out using the passport number, it is also possible to find out the related suspicious person.

Other Modifications

In the examples of the suspicious person management tables T1 to T4 shown in FIGS. 3, 7, 11, and 13, only one record is included. However, this is an example. When two or more suspicious persons are simultaneously tracked in parallel, two or more records for the suspicious people are included in each of the suspicious person management tables T1 to T4. In this case, the monitoring unit 7 only has to determine whether the suspicious person enters the customs area A3 by checking the third image data with each of two or more first image data recorded in the two or more records. Alternatively, the monitoring unit 7 only has to determine whether the suspicious person enters the customs area A3 by checking the passport number read by the second scanner 62 with each of two or more passport numbers recorded in the two or more records.

Another Embodiment

Figure 14:
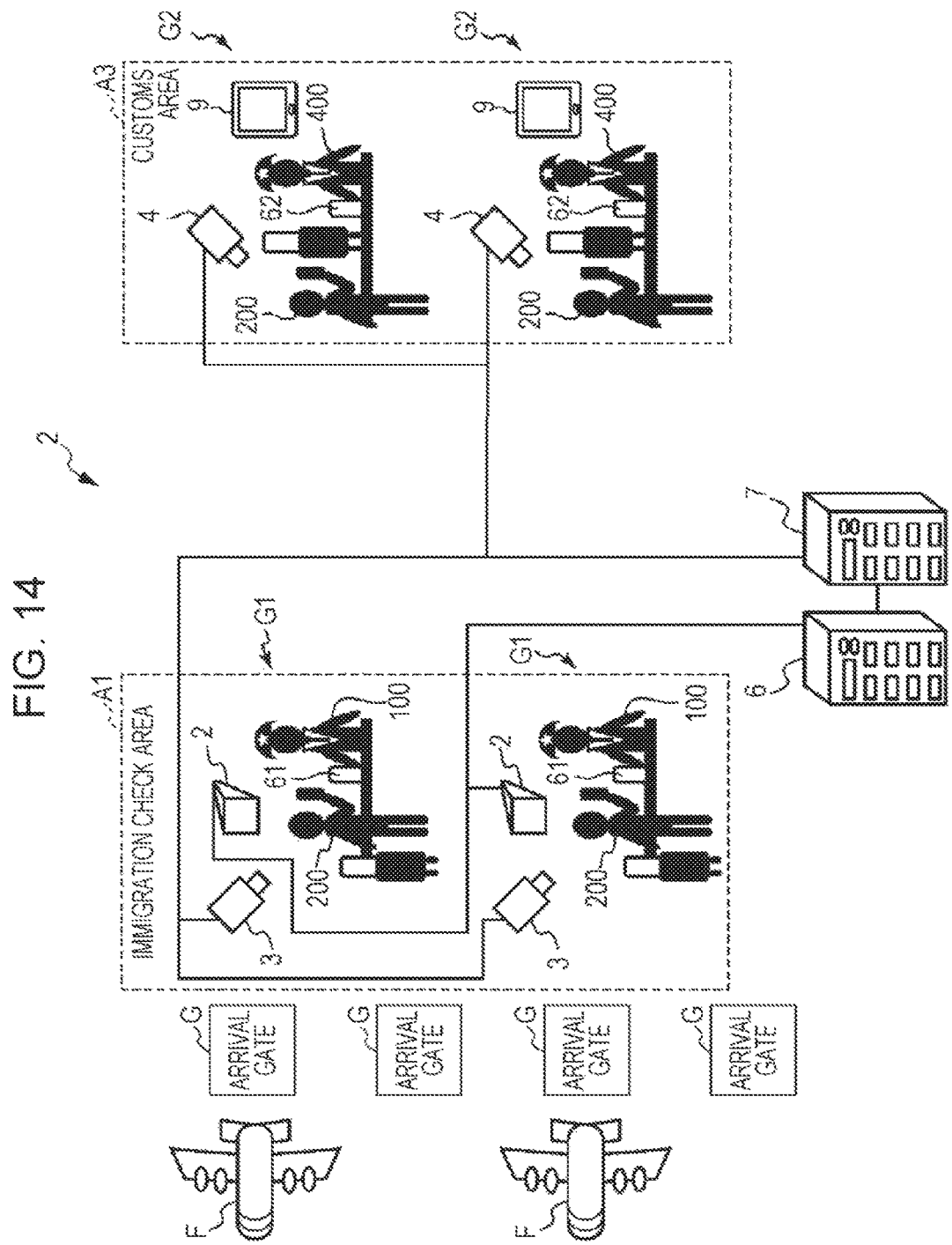
FIG. 14 is a schematic diagram of an airport to which a suspicious person report system according to another embodiment of the present disclosure is applied.

FIG. 14 is a schematic diagram of an airport to which a suspicious person report system 2 according to an embodiment of the present disclosure is applied. The airport is an international airport and includes the arrival gate G, the immigration check area A1, and the customs area A3. The immigration check area A1 is an example of a first region. The customs area A3 is an example of a second region. The arrival gate G is a place where the entrant 200 disembarking from the airplane F arriving from a foreign country passes first. The entrant 200 (an example of a person) passed through the arrival gate G advances to the immigration check area A1 first.

In the immigration check area A1, an immigration check of the entrant 200 is performed. In the immigration check area A1, there is the one or more immigration check gates G1 where the one or more immigration officers 100 are posted. The immigration officer 100 checks a passport of the entrant 200 and questions about a purpose of entry and the like to check whether the entrant 200 is a suspicious person. When determining that the entrant 200 is not a suspicious person, the immigration officer 100 permits the entrant 200 to pass the immigration check gate G1. On the other hand, when determining that the entrant 200 is a suspicious person, the immigration officer 100 does not permit the entrant 200 to pass the immigration check gate G1.

The entrant 200 permitted to pass the immigration check gate G1 moves to the customs area A3 through the passage A2. In the customs area A3, it is inspected whether the entrant 200 intends to smuggle articles prohibited to be brought into the country.

In the customs area A3, there are the one or more customs gates G2 where the one or more customs officers 400 are posted. The customs officer 400 asks the entrant 200 various questions to determine whether the entrant 200 is a suspicious person. When determining that the entrant 200 is a suspicious person, the customs officer 400 checks belongings of the entrant 200. When determining that the entrant 200 is not a suspicious person, the customs officer 400 permits the entrant 200 to pass the customs gate G2. When determining that the entrant 200 is a suspicious person, the customs officer 400 does not permit the entrant 200 to pass the customs gate G2.

In the immigration check area A1, the one or more biometric sensors 2, the one or more first cameras 3, and the one or more first scanners 61 are disposed respectively at the one or more immigration check gates G1. In the customs area A3, the one or more second cameras 4, the one or more second scanners 62, and the one or more warning units 9 are disposed respectively at the one or more customs gates G2. At least one of the first camera 3 and the first scanner 61 is an example of a first acquirer. At least one of the second camera 4 and the second scanner 62 is an example of a second acquirer.

The monitoring unit 7 is communicatively connected to the presuming unit 6. The presuming unit 6 and the monitoring unit 7 are each configured by a computer. The presuming unit 6 is communicatively connected to the biometric sensor 2. The monitoring unit 7 is communicatively connected to the first camera 3, the first scanner 61, the second camera 4, and the second scanner 62. In the example shown in FIG. 14, the presuming unit 6 and the monitoring unit 7 are configured by separate computers and communicatively connected to each other via a communication line such as a LAN. However, this is an example. The presuming unit 6 and the monitoring unit 7 may be configured by one computer. The presuming unit 6 and the monitoring unit 7 may set in an airport or may be set outside the airport. The presuming unit 6 and the monitoring unit 7 may be a cloud server present on a cloud.

Fourth Embodiment

Figure 15:
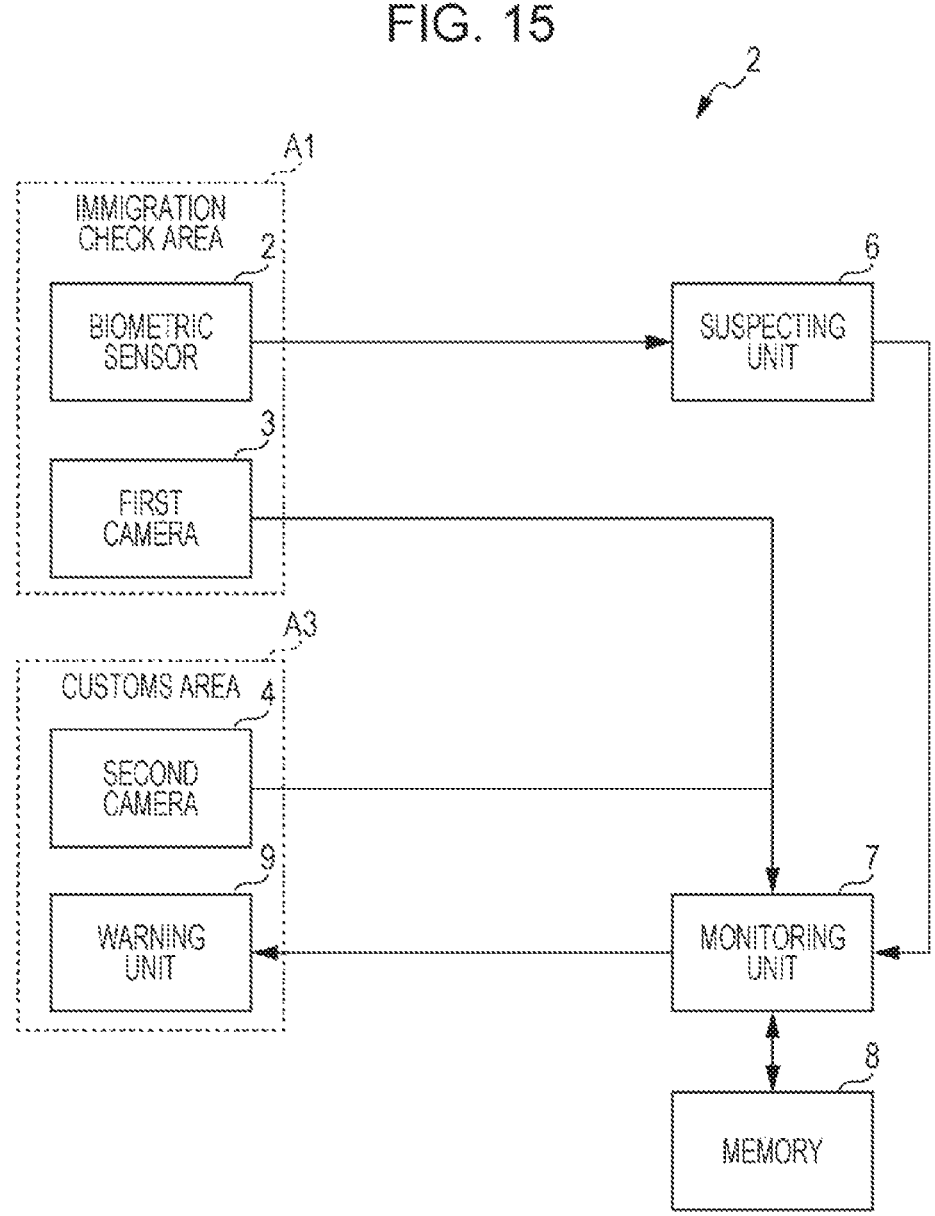
FIG. 15 is a block diagram showing an overall configuration of a suspicious person report system according to a fourth embodiment.

FIG. 15 is a block diagram showing an overall configuration of the suspicious person report system 2 according to a fourth embodiment. The suspicious person report system 2 includes the biometric sensor 2, the first camera 3, the second camera 4, the presuming unit 6, the monitoring unit 7, the memory 8, and the warning unit 9. Note that, in the fourth embodiment, since the first scanner 61 and the second scanner 62 are not used, the first scanner 61 and the second scanner 62 are not shown in FIG. 15.

The biometric sensor 2 includes a measurer that measures biometric data, a processor that performs predetermined signal processing on measurement data measured by the measurer, and a communicator that transmits the biometric data to the presuming unit 6. The predetermined signal processing is, for example, noise removal processing. The biometric sensor 2 detects biometric data of a person who enters the immigration check area A1, As the biometric data, for example, vital data such as a brain wave, a brain blood flow, a pulse wave, a blood pressure, a respiration rate, a body temperature, and perspiration can be adopted.

When the brain wave and the brain blood flow are adopted as the biometric data, a brain wave meter and a brain blood flow meter can be adopted as the biometric sensor 2. When the pulse wave and the blood pressure are adopted as the biometric data, a brain wave meter and a blood pressure meter can be adopted as the biometric sensor 2. When the respiration rate is adopted as the biometric data, a respiration meter can be adopted as the biometric sensor 2. When the body temperature is adopted as the biometric data, a thermometer can be adopted as the biometric sensor 2. When the perspiration is adopted as the biometric data, a perspiration state meter can be adopted as the biometric sensor 2. When a thermal image is adopted as the biometric data, an infrared camera can be adopted as the biometric sensor 2. The biometric sensor 2 may be a biometric sensor that detects biometric data in non-contact with a person or may be a biometric sensor that detects biometric data in contact with the person.

The biometric sensor 2 is communicatively connected to the presuming unit 6 by radio or wire, Under an instruction of the immigration officer 100, when measurement of biometric data is started, the biometric sensor 2 only has to measure biometric data at a fixed sampling interval and transmit a measurement value to the presuming unit 6 in association with a user ID. The user ID is a symbol string uniquely given to identify an individual entrant 200.

As the radio, a wireless LAN such as Bluetooth (registered trademark) or IEEE802.11 can be adopted. As the wire, Ethernet (registered trademark) can be adopted.

The presuming unit 6 calculates, from the biometric data detected by the biometric sensor 2, a stress index indicating a degree of stress of the entrant 200 and, when the stress index is higher than a predetermined reference value, presumes that the entrant 200 is a suspicious person, and transmits a detection signal indicating that the suspicious person is detected to the monitoring unit 7. The detection signal includes a user ID given to the biometric data of the suspicious person.

For example, JP5257525B discloses a technique for performing a frequency analysis of fluctuation in a heartbeat interval from brain wave data to detect stress of a person. Specifically, it is disclosed that the frequency analysis of the heartbeat interval is performed to detect a level HF of a high-frequency peak that occurs at a frequency of about 0.3 Hz and a level LF of a low-frequency peak that occurs at a frequency of about 0.1 Hz and determine that stress of a person is higher as LF/HF is larger.

Therefore, the presuming unit 6 only has to adopt the LF/HF disclosed in the patent as a stress index of the entrant 200 and, when the stress index is larger than a predetermined threshold, determine the entrant 200 as a suspicious person.

JP5735592B discloses that a comfortableness degree of a user is evaluated in ten stages of −5 to +5 from biometric data such as a heart rate, a pulse, and a body temperature.

Therefore, the presuming unit 6 only has to adopt the comfortableness degree disclosed in the patent as a stress index and, when the stress index is larger than a threshold, determine the entrant 200 as a suspicious person. In this case, the presuming unit 6 only has to calculate the stress index from a brain wave, a brain blood flow, a pulse, a blood pressure, a respiration rate, a body temperature, and perspiration.

JP2012-249797A discloses that a value obtained by linearly combining a heart rate, a body temperature, a blood pressure, and perspiration is calculated as a stress value.

Therefore, the presuming unit 6 only has to adopt the stress value disclosed in the publication as a stress index and, when the stress index is larger than a threshold, determine the entrant 200 as a suspicious person.

The presuming unit 6 may calculate a stress index of the entrant 200 from the thermal image data as disclosed in P2003-534864A.

The first camera 3 is provided in the immigration check area A1. The first camera 3 captures an image of each entrant 200 entering a predetermined check position before the immigration check gate G1 and acquires first image data including an image of the entrant 200. The first image data is an example of first identification information. An optical axis and an angle of view of the first camera 3 are set such that the first camera 3 can capture an image of at least the face or the whole body of the entrant 200 entering the check position. Every time a new entrant 200 enters the check position before the immigration check gate G1, the first camera 3 captures an image of the entrant 200 and outputs obtained first image data to the monitoring unit 7.

The second camera 4 is provided in the customs area A3. The second camera 4 captures an image of each entrant 200 entering a predetermined check position before the customs gate G2 and acquires second image data of the entrant 200.

The second image data is an example of second identification information. An optical axis and an angle of view of the second camera 4 are set such that the second camera 4 can capture an image of at least the face or the whole body of the entrant 200 entering the check position. Every time a new entrant 200 enters the check position before the customs gate G2, the second camera 4 captures an image of the entrant 200 and outputs obtained second image data to the monitoring unit 7.

The monitoring unit 7 records the first image data of the person presumed as the suspicious person by the presuming unit 6 in the memory 8.

Specifically, when receiving the detection signal transmitted from the presuming unit 6, the monitoring unit 7 records the first image data captured by the first camera 3 in a suspicious person management table T5 included in the memory 8 in association with a user ID included in the detection signal.

FIG. 16 is a diagram showing an example of the suspicious person management table T5 according to the fourth embodiment. The suspicious person management table T5 is a two-dimensional table in which user IDs and image data are recorded in association with each other. A user ID issued by the monitoring unit 7 is recorded in a field of "user ID". First image data concerning the user ID is recorded in a field of "image data".

Referring back to FIG. 15, every time the second image data is transmitted from the second camera 4, the monitoring unit 7 checks the second image data with the first image data recorded in the suspicious person management table T5 and determines whether the suspicious person is included in the second image data.

Specifically, the monitoring unit 7 calculates similarity of a feature value of the suspicious person extracted from the first image data and a feature value of a person extracted from the second image data and, if the calculated similarity is equal to or larger than a specified value, determines that the suspicious person is included in the second image data. As the specified value, a predetermined value for regarding the two of them as the same person can be adopted.

As the feature value of the suspicious person, a feature value of the face of the suspicious person may be adopted or a feature value of clothes worn by the suspicious person may be adopted. The monitoring unit 7 records the first image data of the suspicious person in the suspicious person management table T5. However, this is an example. The feature value of the suspicious person extracted from the first image data may be recorded. The same applies in embodiments explained below.

When determining that the suspicious person is included in the second image data, the monitoring unit 7 causes the warning unit 9 to emit a warning.

The warning unit 9 is configured by a display device set in the customs area A3. As the display device, a liquid crystal display, an organic EL display, and the like can be adopted. A display surface of the display device faces the customs officer 400. The display device is disposed such that only the customs officer 400 can visually recognize an image.

The warning unit 9 only has to emit a warning by, for example, displaying a face image of the suspicious person or a whole body image of the suspicious person to emit the warning. In this case, the warning unit 9 only has to receive image data of the suspicious person from the monitoring unit 7 and display the image data of the suspicious person. As a warning method by the warning unit 9, an aspect in which the face image and the whole body image are displayed on the display device is explained above. However, this is an example. For example, the warning unit 9 may be configured by an LED lamp and turn on the LED lamp to emit the warning. Alternatively, the warning unit 9 may be configured by a speaker and emit the warning by outputting, from the speaker, a voice message for informing that the suspicious person enters the customs area A3.

The memory 8 is configured by a nonvolatile rewritable storage device mounted on a computer communicatively connected to the monitoring unit 7 and stores the suspicious person management table T5 and the like. The memory 8 may be connected to the monitoring unit 7 via a communication line such as a LAN or may be provided on the cloud. The memory 8 may be communicatively connected to the presuming unit 6. The memory 8 may be configured by the storage device of the monitoring unit 7.

<Sequence>

Figure 18:
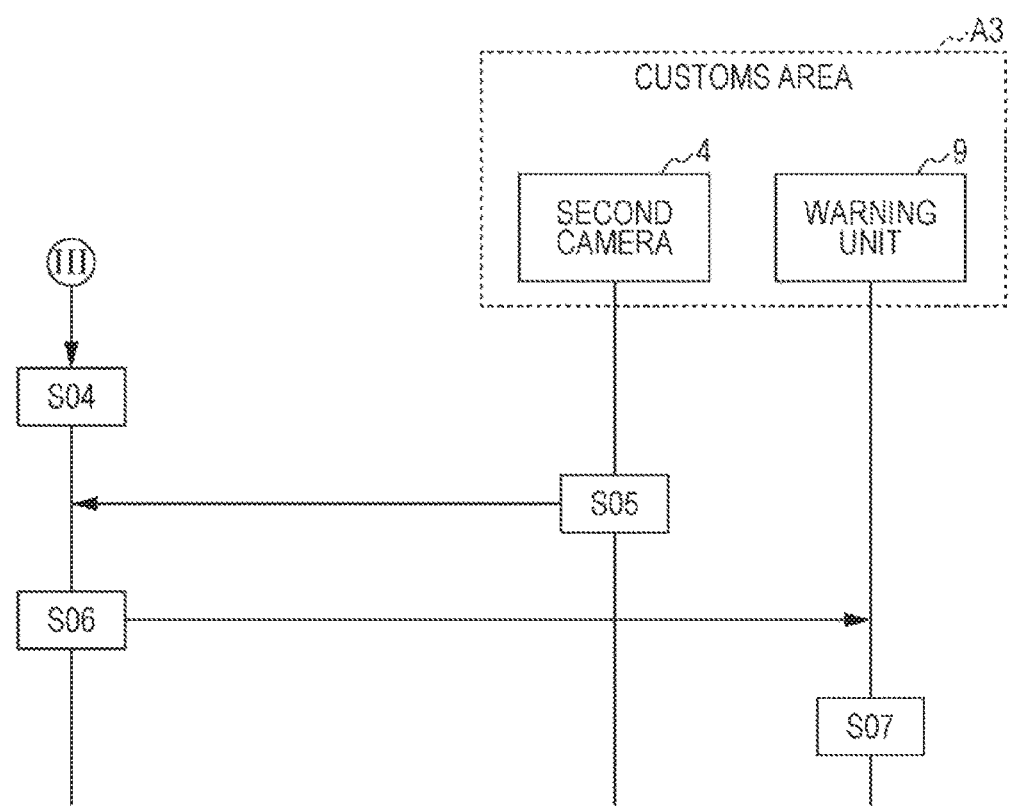
FIG. 18 is a sequence chart following FIG. 17.

The operation of the suspicious person report system 2 is explained. FIG. 17 is a sequence chart showing the operation of the suspicious person report system 2. FIG. 18 is a sequence chart following FIG. 17.

(S01) The biometric sensor 2 measures biometric data of the entrant 200 entering the check position in the immigration check area A1. The biometric sensor 2 gives a user ID to each entrant 200 and transmits the user ID to the presuming unit 6 in association with biometric data. Note that, when the biometric sensor 2 is configured by a contact-type biometric sensor, the biometric sensor 2 is attached to the entrant 200 by the immigration officer 100 or another officer. The biometric sensor 2 only has to start measurement of biometric data, for example, with an input of a measurement start instruction from the immigration officer 100 as a trigger, measure biometric data at a fixed sampling interval until a measurement end instruction is input from the immigration officer 100, and transmit the measured biometric data to the presuming unit 6 in association with the user ID.

(S02) In parallel to the processing in S01, the first camera 3 captures an image of the entrant 200 being checked, acquires first image data, and transmits the first image data to the monitoring unit 7. The first camera 3 only has to capture an image of an entrant, for example, with an input of an image capture instruction from the immigration officer 100 as a trigger and transmit the acquired first image data to the monitoring unit 7.

(S03) The presuming unit 6 calculates a stress index from the biometric data received from the biometric sensor 2 and determines whether the entrant 200 is a suspicious person. When determining that the entrant 200 is a suspicious person, the presuming unit 6 generates a detection signal including a user ID associated with biometric data of the suspicious person and transmits the detection signal to the monitoring unit 7. On the other hand, when determining that the entrant 200 is not a suspicious person, the presuming unit 6 ends the processing.

(S04) When receiving the detection signal, the monitoring unit 7 records the first image data transmitted from the first camera 3 in the same period in the suspicious person management table T5 in association with the user ID of the suspicious person included in the detection signal. Consequently, the first image data of the suspicious person is recorded. The monitoring unit 7 only has to record first image data transmitted within a fixed period around a time of reception of the detection signal in the suspicious person management table T5 as the first image data of the suspicious person. As the fixed period, a period estimated to be consumed for measurement of biometric data and capturing of first image data concerning the same person is adopted.

(S05) The second camera 4 captures an image of the entrant 200 entering the check position in the customs area A3, acquires second image data of the entrant 200, and transmits the second image data to the monitoring unit 7. The second camera 4 only has to capture an image of the entrant 200, for example, with an input of an image capture instruction from the customs officer 400 as a trigger, and transmit the second image data to the monitoring unit 7.

(S06) The monitoring unit 7 checks the second image data captured by the second camera 4 with the first image data of the suspicious person recorded in the suspicious person management table T5 and determines whether the suspicious person is included in the second image data.

(S07) When the monitoring unit 7 determines that the suspicious person is included in the second image data, the warning unit 9 displays a face image or a whole body image of the suspicious person on the display device. Consequently, the customs officer 400 can recognize that the entrant 200 in front of the customs officer 400 is the suspicious person and can take necessary measures. Examples of the necessary measures include a measure for opening a bag carried by the suspicious person and inspecting belongings of the suspicious person in detail and a measure for moving the suspicious person to another interrogation room and interrogating the suspicious person.

As explained above, with the suspicious person report system 2, the biometric data and the first image data of the entrant 200 entering the immigration check area A1 are acquired and, if the stress index obtained from the biometric data is higher than the reference value, the entrant 200 is presumed as a suspicious person, and the first image data is recorded in the memory 8.

When the suspicious person indicated by the first image data recorded in the memory 8 is included in the second image data obtained by capturing an image of the entrant 200 entering the customs area A3 with the second camera 4, the warning is emitted.

Therefore, even if the immigration officer 100 permits passage of the suspicious person in the immigration check area A1, since the warning is emitted when the suspicious person enters the customs area A3, it is possible to find out the suspicious person.

As explained above, with the suspicious person report system 2, it is possible to find out the suspicious person by effectively using the immigration check area A1 and the customs area A3 provided apart from each other where an entrant is obliged to pass in order in the airport.

Fifth Embodiment

Figure 19:
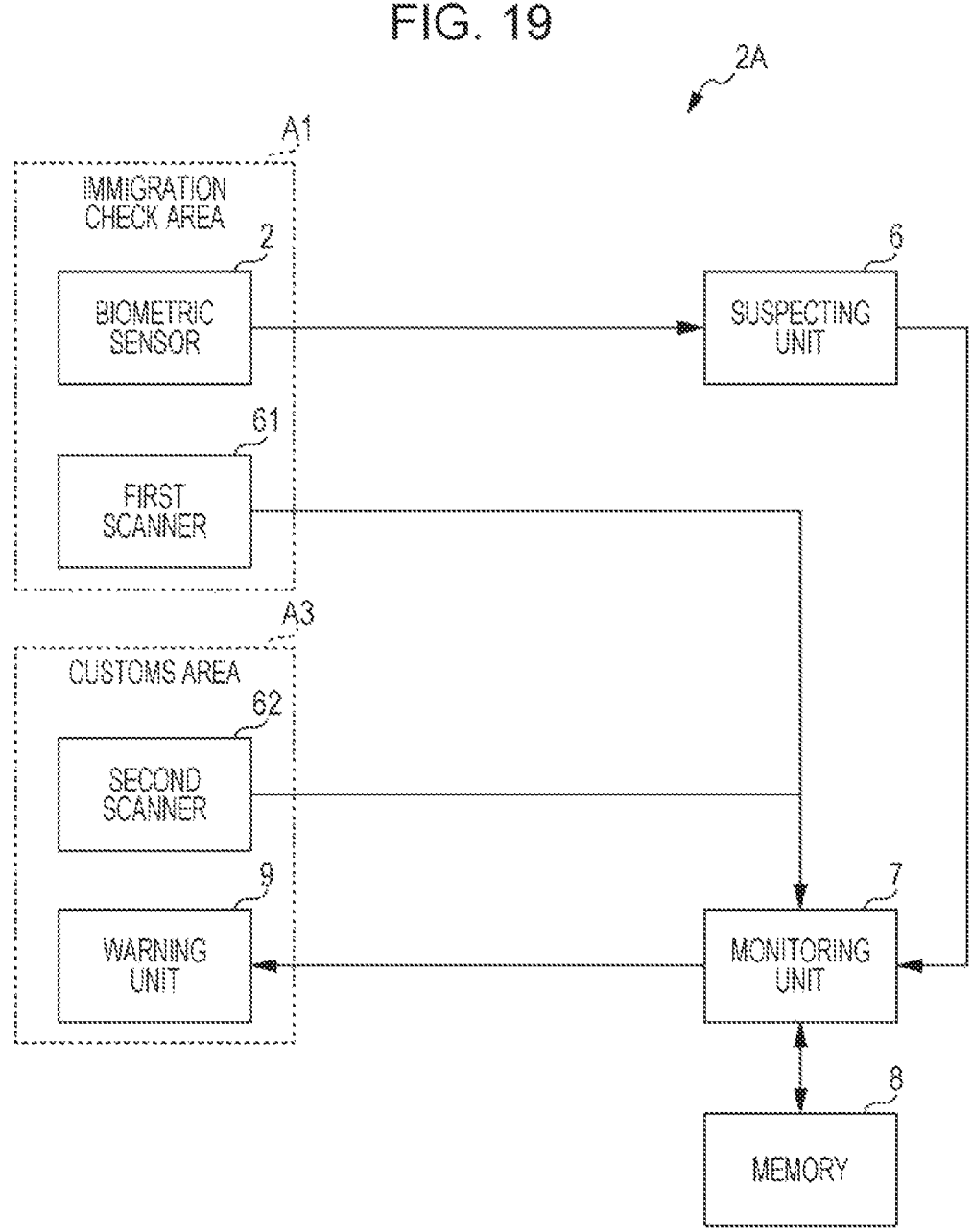
FIG. 19 is a block diagram showing an overall configuration of a suspicious person report system according to a fifth embodiment.

FIG. 19 is a block diagram showing an overall configuration of a suspicious person report system 2A according to a fifth embodiment. The suspicious person report system 2A is characterized by reporting a suspicious person using a passport number of a passport carried by the entrant 200. FIG. 19 is different from FIG. 15 in that the first scanner 61 is provided in the immigration check area A1 instead of the first camera 3 and the second scanner 62 is provided in the customs area A3 instead of the second camera 4. Note that, in the fifth embodiment, components same as the components in the fourth embodiment are denoted by the same reference numerals and signs and explanation of the components is omitted.

The first scanner 61 is provided in the immigration check area A1. The first scanner 61 reads, according to an instruction of the immigration officer 100, a passport number described in a passport presented by the entrant 200 in the immigration check gate G1 and transmits the passport number to the monitoring unit 7. The passport number read by the first scanner 61 is an example of a first passport number. Note that, in the case of a passport in which a passport number is stored in an electronic chip, the first scanner 61 only has to acquire the passport number by communicating with the electronic chip. The same applies to the second scanner 62.

The second scanner 62 is provided in the customs area A3. The second scanner 62 reads, according to an instruction of the customs officer 400, a passport number described in a passport presented by the entrant 200 before the customs gate G2 and transmits the passport number to the monitoring unit 7. The passport number read by the second scanner 62 is an example of a second passport number.

When receiving a detection signal from the presuming unit 6, the monitoring unit 7 records the passport number transmitted from the first scanner 61 in the same period in a suspicious person management table T6 (FIG. 20) included in the memory 8 as a passport number of the suspicious person.

When the passport number of the suspicious person recorded in the suspicious person management table T6 and the passport number read by the second scanner 62 match each other, the monitoring unit 7 causes the warning unit 9 to emit a warning.

Figures 20, 21:
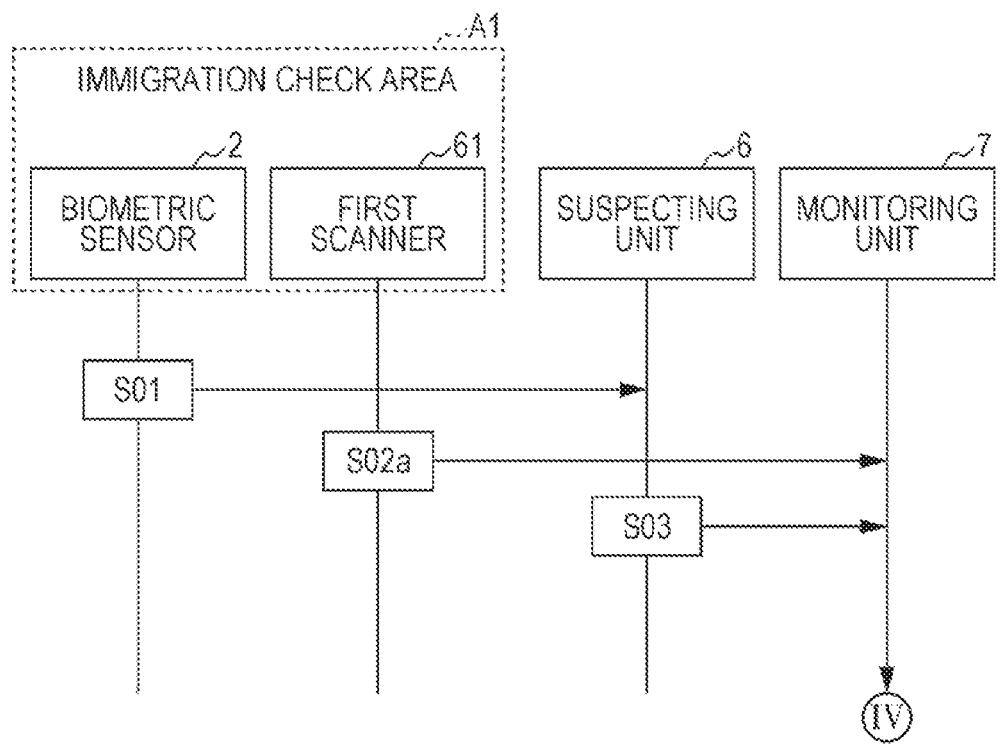
FIG. 20 is a diagram showing an example of a suspicious person management table according to the fifth embodiment.
FIG. 21 is a sequence chart showing the operation of the suspicious person report system according to the fifth embodiment.

FIG. 20 is a diagram showing an example of the suspicious person management table T6 according to the fifth embodiment. The suspicious person management table T6 is different from the suspicious person management table T5 in that a passport number is provided instead of the user ID and image data is omitted. Since the passport number is uniquely given to the individual entrant 200, the passport number is capable of uniquely identifying a suspicious person. Therefore, in the fifth embodiment, the passport number is adopted instead of the user ID.

Note that, in the fifth embodiment, since a user ID is not used, the biometric sensor 2 does not need to issue a user ID. Therefore, it is possible to reduce a processing load on the biometric sensor 2.

<Sequence>

Figure 22:
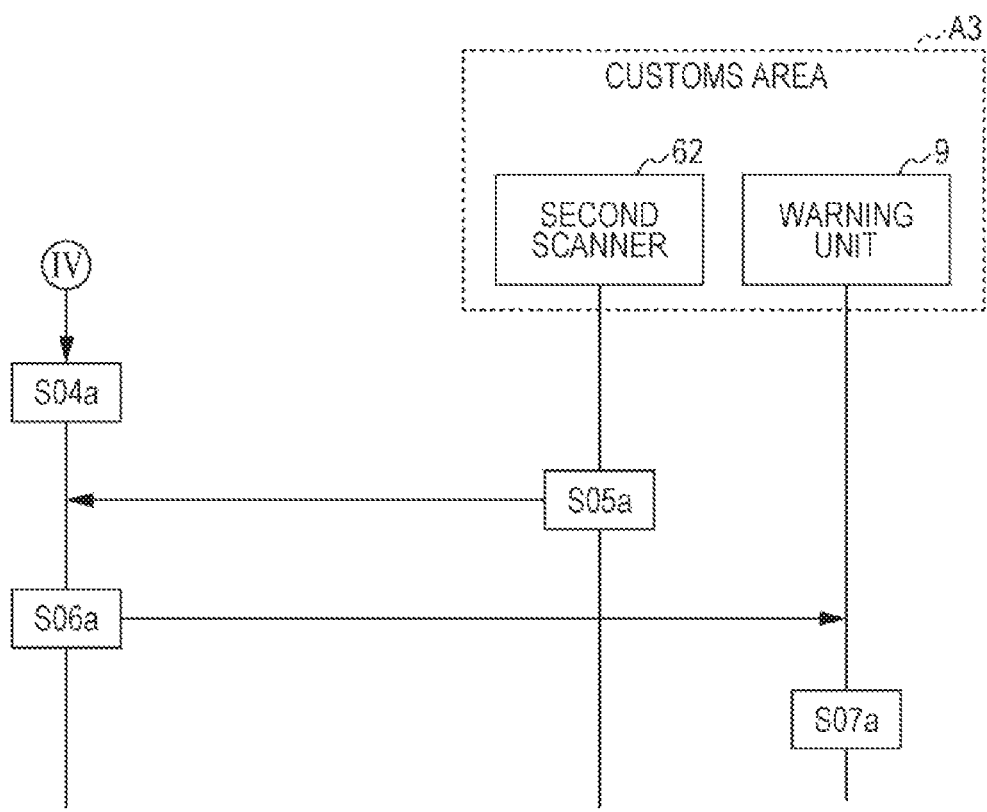
FIG. 22 is a sequence chart following FIG. 21.

FIG. 21 is a sequence chart showing the operation of the suspicious person report system 2A according to the fifth embodiment, FIG. 22 is a sequence chart following FIG. 21.

Note that, in FIGS. 21 and 22, kinds of processing same as the kinds of processing shown in FIGS. 17 and 18 are denoted by the same reference signs and explanation of the kinds of processing is omitted.

(S02a) S02a is processing performed in parallel to S01. The first scanner 61 reads a passport number of the entrant 200 and transmits the passport number to the monitoring unit 7.

(S04a) S04a is processing following S03. When receiving a detection signal, the monitoring unit 7 records the passport number transmitted from the first scanner 61 in the suspicious person management table T6. Consequently, the passport number of the suspicious person is recorded. The monitoring unit 7 only has to record a passport number transmitted within a fixed period around a time of the reception of the detection signal in the suspicious person management table T6 as the passport number of the suspicious person. As the fixed period, a period estimated to be consumed for measurement of biometric data and acquisition of a passport number of the same person is adopted.

(S05a) S05a is processing following S04a. The second scanner 62 reads, according to an instruction of the customs officer 400, a passport number presented by the entrant 200 entering the check position in the customs area A3 and transmits the passport number to the monitoring unit 7.

(S06a) S06a is processing following S05a. The monitoring unit 7 checks whether the passport number of the suspicious person recorded in the suspicious person management table T6 and the passport number read by the second scanner 62 match each other.

When the monitoring unit 7 determines that the two passport numbers match each other, the warning unit 9 emits a warning (S07a). When the two passport numbers do not match each other, the processing ends. Since image data of the suspicious person is not acquired, the warning unit 9 cannot display image data of the suspicious person. Therefore, the warning unit 9 may emit a warning by turning on the LED lamp or may emit a warning by outputting, from the speaker, a voice message for informing that the suspicious person intrudes into the customs area A3.

As explained above, with the suspicious person report system 2A, the passport number of the suspicious person is acquired in the immigration check area A1 and recorded in the suspicious person management table T6. Therefore, the suspicious person report system 2A can find out the suspicious person in the customs area A3 by checking the passport number acquired in the customs area A3 with the passport number recorded in the suspicious person management table T6.

Sixth Embodiment

Figure 23:
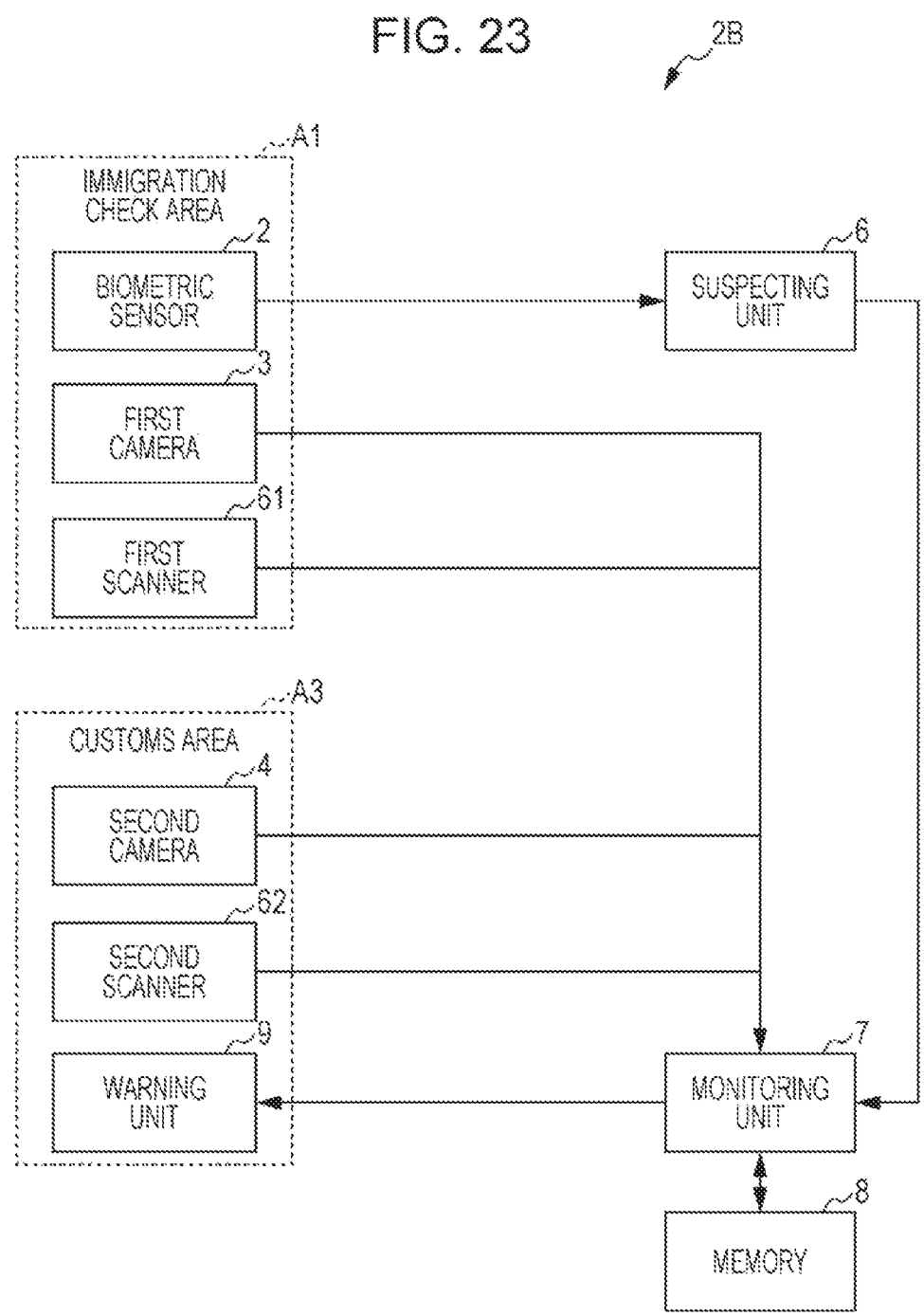
FIG. 23 is a block diagram showing an overall configuration of a suspicious person report system according to a sixth embodiment.

FIG. 23 is a block diagram showing an overall configuration of a suspicious person report system 2B according to a sixth embodiment. The suspicious person report system 2B is characterized by performing a warning by displaying a face image of a suspicious person in the suspicious person report system 2A in the fifth embodiment.

FIG. 23 is different from FIG. 19 in that the first camera 3 is further provided in the immigration check area A1 and the second scanner 62 is further provided in the customs area A3. Note that, in the sixth embodiment, components same as the components in the fifth and sixth embodiments are denoted by the same reference numerals and signs and explanation of the components is omitted.

When receiving a detection signal from the presuming unit 6, the monitoring unit 7 records a passport number transmitted from the first scanner 61 in the same period in a suspicious person management table T7 (FIG. 24) included in the memory 8 in association with first image data acquired by the first camera 3.

FIG. 24 is a diagram showing an example of the suspicious person management table T7 according to the sixth embodiment. The suspicious person management table T7 is different from the suspicious person management table T6 in that a field of image data is provided in association with a passport number. For example, the warning unit 9 is capable of emitting a warning using the image data.

When a passport number of a suspicious person recorded in the suspicious person management table T7 and a passport number read by the second scanner 62 match each other, the monitoring unit 7 causes the warning unit 9 to emit a warning.

<Sequence>

Figure 26:
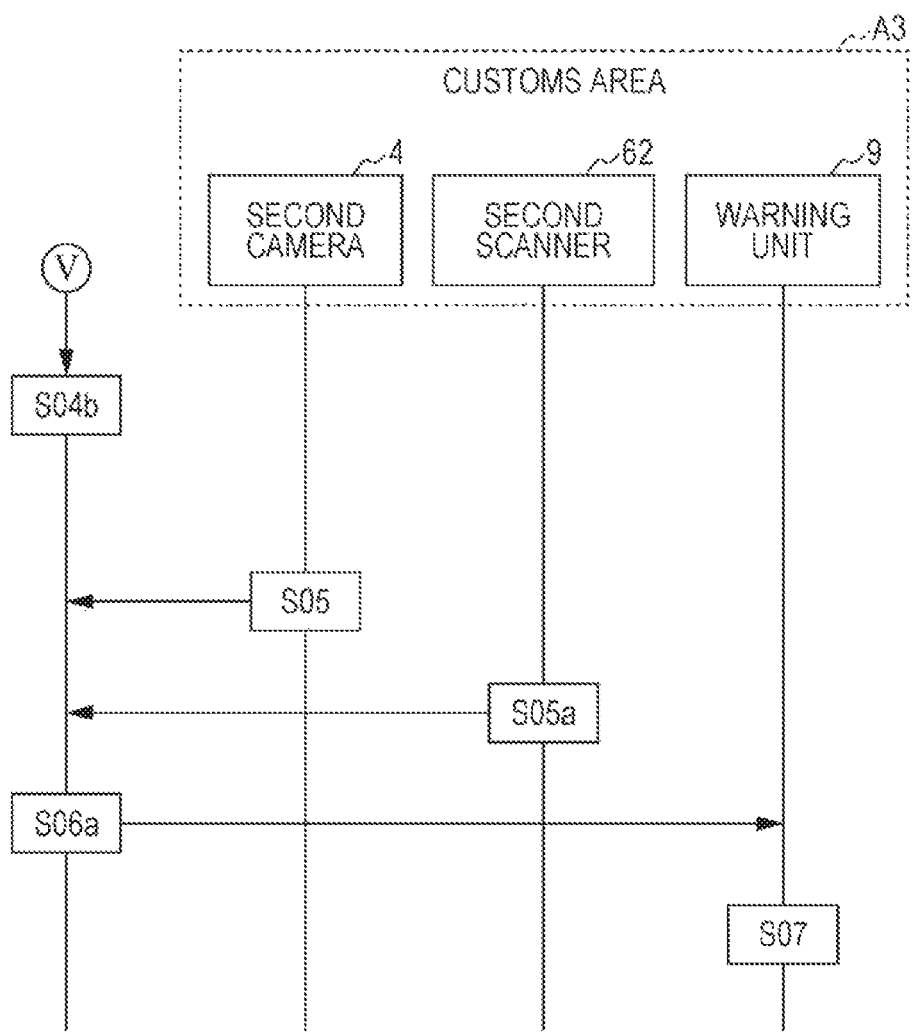
FIG. 26 is a sequence chart following FIG. 25.

FIG. 25 is a sequence chart showing the operation of the suspicious person report system 2B according the sixth embodiment. FIG. 26 is a sequence chart following FIG. 25. Note that, in FIGS. 25 and 26, kinds of processing same as the kinds of processing shown in FIGS. 21 and 22 are denoted by the same reference signs and explanation of the kinds of processing is omitted.

(S02, S02a) S02 is the processing shown in FIG. 17 in which the first camera 3 captures an image of the entrant 200 being checked, acquires first image data, and transmits the first image data to the monitoring unit 7. S02a is the processing shown in FIG. 8 in which the first scanner 61 reads a passport number of the entrant 200 and transmits the passport number to the monitoring unit 7. S02 and S02a are performed in parallel to the processing in S01.

(S04b) S04b is processing following S03. When receiving a detection signal, the monitoring unit 7 records the first image data transmitted from the first camera 3 in the suspicious person management table T7 in association with the passport number transmitted from the first scanner 61. Consequently, first image data of a suspicious person is recorded together with a passport number of the suspicious person. The monitoring unit 7 only has to record first image data and a passport number transmitted within a fixed period around a time of the reception of the detection signal in the suspicious person management table T7 as the first image data and the passport number of the suspicious person. As the fixed period, a period estimated to be consumed for measurement of biometric data, capturing of first image data, and acquisition of a passport number of the same person is adopted.

(S05, S05a) S05 is the processing shown in FIG. 18 in which the second camera 4 captures an image of the entrant 200 entering the check position in the customs area A3, acquires second image data of the entrant 200, and transmits the second image data to the monitoring unit 7. S05a is the processing shown in FIG. 22 in which the second scanner 62 reads, according to an instruction of the customs officer 400, a passport number present by the entrant 200 entering the check position in the customs area A3 and transmits the passport number to the monitoring unit 7. S05 and S05a are performed in parallel.

(S06a) S06a is processing following S05a. The monitoring unit 7 checks whether the passport number of the suspicious person recorded in the suspicious person management table T7 and the passport number read by the second scanner 62 match each other.

(S07) When the monitoring unit 7 determines that the suspicious person is included in the second image data, the warning unit 9 displays a face image or a whole body image of the suspicious person on the display device. In this case, the warning unit 9 may display the first image data of the suspicious person recorded in the memory 8 in S02 on the display device or may display the second image data of the suspicious person captured by the second camera 4 in S05 on the display device. Consequently, the customs officer 400 can recognize that the entrant 200 in front of the customs officer 400 is a suspicious person and can take necessary measures.

As explained above, with the suspicious person report system 2B according to the sixth embodiment, the customs officer 400 can easily find out the suspicious person since the face image of the suspicious person is displayed on the display device.

Note that, in the sixth embodiment, the monitoring unit 7 finds out the suspicious person by checking the passport number acquired by the first scanner 61 and the passport number acquired by the second scanner 62. However, this is an example. As in the fourth embodiment, the monitoring unit 7 may find out the suspicious person by checking the first image data acquired by the first camera 3 and the second image data acquired by the second camera 4.

When an aspect is adopted in which the warning unit 9 displays the face image of the suspicious person on the display device using the first image data acquired by the first camera 3, the second camera 4 is unnecessary in the customs area A3.

Modification

In the examples of the suspicious person management tables T5 to T7 shown in FIGS. 16, 20, and 24, only one record is included. However, this is an example. When two or more suspicious persons are simultaneously detected in parallel, two or more records for the suspicious people are included in the suspicious person management tables T5 to T7. In this case, the monitoring unit 7 only has to determine whether the suspicious person is included in the second image data by checking the second image data with each of two or more first image data recorded in the two or more records. Alternatively, the monitoring unit 7 may check the passport number read by the second scanner 62 with each of two or more passport numbers recorded in the two or more records.

The technique of the present disclosure is useful for security measures in an airport, a port, and the like.

What is claimed is:

1. A suspicious person report system, comprising:
   a biometric sensor that detects biometric data of a person in a first region;
   a presuming unit that calculates, from the biometric data, a stress index indicating a degree of stress and presumes that the person is a suspicious person when the calculated stress index is higher than a predetermined reference value;
   a first camera that acquires first image data including an image of the person in the first region;
   a second camera that acquires second image data including an image of the person in a second region, the second region being a route that the person passes after leaving the first region before entering a third region;
   a monitoring unit that checks the second image data with the first image data corresponding to the person presumed as the suspicious person to thereby track the person presumed as the suspicious person in the second region and determine whether or not the person presumed as the suspicious person enters the third region; and
   a warning unit that emits a warning when the monitoring unit determines that the person presumed as the suspicious person enters the third region.

2. The suspicious person report system according to claim 1, further comprising a third camera that acquires third image data including an image of the person in the third region, wherein
   the monitoring unit checks the third image data with the first image data and determines that the person presumed as the suspicious person enters the third region when the third image data includes an image of the person presumed as the suspicious person.

3. The suspicious person report system according to claim 2, further comprising a memory that records the first image data corresponding to the person presumed as the suspicious person, wherein
   the monitoring unit checks the third image data with the first image data recorded in the memory and determines that the person presumed as the suspicious person enters the third region when the third image data includes an image of the person presumed as the suspicious person.

4. The suspicious person report system according to claim 1, further comprising:
   a first acquirer that acquires a passport number of the person in the first region; and
   a second acquirer that acquires a passport number of the person in the third region, wherein
   when the passport number acquired by the second acquirer matches the passport number acquired by the first acquirer from the person presumed as the suspicious person, the monitoring unit determines that the person presumed as the suspicious person enters the third region.

5. The suspicious person report system according to claim 4, further comprising a memory that records the passport number corresponding to the person presumed as the suspicious person, the passport number being acquired by the first acquirer, wherein
   when the passport number acquired by the second acquirer matches the passport number recorded in the memory, the monitoring unit determines that the person presumed as the suspicious person enters the third region.

6. The suspicious person report system according to claim 1, wherein
   the first region is an immigration check area, and
   the third region is a customs area.

7. The suspicious person report system according to claim 6, wherein the warning unit emits the warning to an officer in the customs area.

8. The suspicious person report system according to claim 1, further comprising a third camera that acquires third image data including an image of the person in the third region, wherein
   when detecting, in the second image data, a person approaching the person presumed as the suspicious person within a first distance, the monitoring unit presumes that the approaching person is a related suspicious person, checks the third image data with the second image data including an image of the person presumed as the related suspicious person and determines that the person presumed as the related suspicious person enters the third region when the third image data includes an image of the person presumed as the related suspicious person, and
   when the monitoring unit determines that the person presumed as the related suspicious person enters the third region, the warning unit emits a warning.

9. The suspicious person report system according to claim 1, further comprising a third camera that acquires third image data including an image of the person in the third region, wherein
   when detecting, in the second image data, that a different person approaching the person presumed as the suspicious person within a first distance performs a specific action, the monitoring unit presumes that the different person performing the specific action is a related suspicious person, checks the third image data with the second image data including an image of the different person presumed as the related suspicious person and determines that the different person presumed as the related suspicious person enters the third region when the third image data includes an image of the different person presumed as the related suspicious person, and when the monitoring unit determines that the person presumed as the related suspicious person enters the third region, the warning unit emits a warning.

10. The suspicious person report system according to claim 1, further comprising a third camera that acquires third image data including an image of the person in the third region, wherein
when detecting, in the second image data, that any of belongings of the person presumed as the suspicious person is handed to a different person, the monitoring unit presumes that the different person is a related suspicious person, checks the third image data with the second image data including an image of the different person presumed as the related suspicious person and, when the third image data includes an image of the different person presumed as the related suspicious person, determines that the different person presumed as the related suspicious person enters the third region, and
when the monitoring unit determines that the person presumed as the related suspicious person enters the third region, the warning unit emits a warning.

11. The suspicious person report system according to claim 1, wherein
the first image data includes a face image of the person; and
the warning unit displays the face image of the person presumed as the suspicious person.

12. The suspicious person report system according to claim 1, further comprising a memory that records the first image data corresponding to the person presumed as the suspicious person, wherein
the monitoring unit checks the second image data with the first image data recorded in the memory to thereby track the person presumed as the suspicious person in the second region.

13. The suspicious person report system according to claim 1, wherein the biometric sensor is a contact based sensor.

14. The suspicious person report system according to claim 1, wherein the biometric data includes at least one of a brain wave, a brain blood flow, a pulse wave, a blood pressure, a respiration rate, a body temperature, or a perspiration.

15. A suspicious person report method, comprising:
detecting biometric data of a person with a biometric sensor in a first region;
calculating, from the biometric data, a stress index indicating a degree of stress,
presuming that the person is a suspicious person when the calculated stress index is higher than a predetermined reference value;
acquiring first image data including an image of the person in the first region;
acquiring second image data including an image of the person in a second region, the second region being a route that the person passes after leaving the first region before entering a third region;
checking the second image data with the first image data corresponding to the person presumed as the suspicious person to thereby track the person presumed as the suspicious person in the second region and determine whether or not the person presumed as the suspicious person enters the third region; and
emitting a warning when the monitoring unit determines that the person presumed as the suspicious person enters the third region.

* * * * *